United States Patent
Horie et al.

(10) Patent No.: US 10,335,358 B2
(45) Date of Patent: Jul. 2, 2019

(54) HAIR COSMETIC

(71) Applicant: KAO CORPORATION, Tokyo (JP)

(72) Inventors: Yu Horie, Koto-ku (JP); Kenji Hozumi, Wakayama (JP); Takashi Mizooku, Wakayama (JP); Hiroto Tanamachi, Yachiyo (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/895,997

(22) PCT Filed: Jun. 4, 2014

(86) PCT No.: PCT/JP2014/064881
§ 371 (c)(1),
(2) Date: Dec. 4, 2015

(87) PCT Pub. No.: WO2014/196579
PCT Pub. Date: Dec. 11, 2014

(65) Prior Publication Data
US 2016/0120783 A1 May 5, 2016

(30) Foreign Application Priority Data

Jun. 5, 2013 (JP) .................................. 2013-119230
Jun. 5, 2013 (JP) .................................. 2013-119231

(51) Int. Cl.
| | | |
|---|---|---|
| *A61K 8/73* | (2006.01) | |
| *A61K 8/81* | (2006.01) | |
| *A61Q 5/08* | (2006.01) | |
| *A61Q 5/10* | (2006.01) | |
| *A61Q 5/12* | (2006.01) | |
| *A61Q 5/02* | (2006.01) | |
| *A61Q 5/06* | (2006.01) | |

(52) U.S. Cl.
CPC .............. *A61K 8/731* (2013.01); *A61K 8/732* (2013.01); *A61K 8/737* (2013.01); *A61K 8/817* (2013.01); *A61Q 5/12* (2013.01); *A61K 2800/5424* (2013.01); *A61K 2800/5426* (2013.01); *A61K 2800/594* (2013.01); *A61K 2800/882* (2013.01); *A61Q 5/02* (2013.01); *A61Q 5/06* (2013.01); *A61Q 5/065* (2013.01); *A61Q 5/08* (2013.01); *A61Q 5/10* (2013.01)

(58) Field of Classification Search
CPC ........ A61K 8/732; A61K 8/737; A61K 8/817; A61Q 5/12
See application file for complete search history.

(56) References Cited

U.S. PATENT DOCUMENTS 5,393,305 A 2/1995 Cohen et al.
5,534,248 A 7/1996 Matsuo et al.

2006/0292104 A1 12/2006 Guskey et al.
2006/0293197 A1 12/2006 Uehara et al.
2012/0207689 A1 8/2012 Konno et al.

FOREIGN PATENT DOCUMENTS

| | | |
|---|---|---|
| EP | 0 640 335 A2 | 3/1995 |
| EP | 0 640 335 A3 | 3/1995 |
| JP | 06-172135 | 6/1994 |
| JP | 9-110901 A | 4/1997 |
| JP | 10 95714 | 4/1998 |
| JP | 10 287535 | 10/1998 |
| JP | 2000-053524 | 2/2000 |
| JP | 2000-327541 | 11/2000 |
| JP | 2002 193772 | 7/2002 |
| JP | 2004-269400 | 9/2004 |
| JP | 2004 323423 | 11/2004 |
| JP | 2005 36014 | 2/2005 |
| JP | 2005 206562 | 8/2005 |
| JP | 2006 282674 | 10/2006 |
| JP | 2007-291016 | 11/2007 |
| JP | 2008 201727 | 9/2008 |
| JP | 2008 285415 | 11/2008 |
| JP | 2008 290953 | 12/2008 |

(Continued)

OTHER PUBLICATIONS

Extended European Search Report dated Oct. 20, 2016 in European Patent Application No. 14807141.8.

(Continued)

*Primary Examiner* — Alma Pipic
(74) *Attorney, Agent, or Firm* — Oblon, McClelland, Maier & Neustadt, L.L.P.

(57) ABSTRACT

A hair cosmetic comprising the following ingredients (A) and (B): (A) a cationic polymer having a charge density of 5.0 to 7.0 meq/g and (B) an anionic polysaccharide derivative wherein a part of the H atoms of the OH group of a polysaccharide compound having the constituent unit described below are substituted with a —(CH$_2$)$_m$COO$^-$ group (m is an integer of 1 to 5) at an average substitution degree of 0.5 to 2.0 per constituent unit, and wherein optionally a part of the H atoms of the remaining —OH groups are substituted with C$_{1-40}$ alkyl groups and/or alkylene groups, wherein the viscosity of the ingredient (B) in a 2 mass % aqueous solution (25° C.) is 0.5 to 800 mPa·s

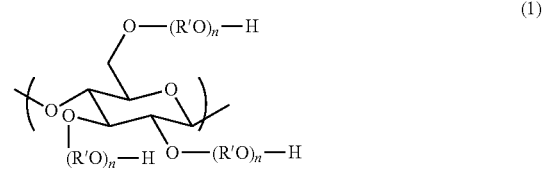

(1)

wherein R' represents a C$_{2-4}$ alkylene group optionally substituted with an —OH group, and n represents a number by which the average number of added moles of R'O per constituent unit is 0 to 10.

10 Claims, No Drawings

(56) References Cited

FOREIGN PATENT DOCUMENTS

| JP | 2008 543949 | 12/2008 |
|----|-------------|---------|
| JP | 2008 546806 | 12/2008 |
| JP | 2009 504661 | 2/2009 |
| JP | 2012-106960 | 6/2012 |
| JP | 2012 136464 | 7/2012 |
| JP | 2013-056846 | 3/2013 |
| JP | 2015-13854 A | 1/2015 |
| JP | 2015 151373 | 8/2015 |
| JP | 2015 151374 | 8/2015 |
| JP | 2015-166332 A | 9/2015 |
| JP | 2015-166333 A | 9/2015 |
| WO | 2011 059027 | 5/2011 |
| WO | 2012 150710 | 11/2012 |

OTHER PUBLICATIONS

International Search Report dated Aug. 19, 2014 in PCT/JP14/064881 Filed Jun. 4, 2014.

HAIR COSMETIC

FIELD OF THE INVENTION

The present invention relates to a hair cosmetic.

BACKGROUND OF THE INVENTION

Hair is damaged by hair color treatment, perming treatment, heating by a hair drier, exposure to sunlight and weathering such as daily hair-washing action. As a result, good touch and beautiful appearance originally possessed by healthy hair are damaged. As a method to resolve this problem, known is a method of applying a hair cosmetic whereby to render a conditioning ingredient to remain on the hair surface or the hair surface layer (for example, see Patent Documents 1 to 3).

However, with conventional conditioning ingredients, persistence of the effects was not sufficient, and there were proposed some techniques for keeping the effect of ingredients remaining on hair despite a certain degree of repetitive hair-washings. For example, known are a hair treatment agent using a specific polymer (for example, see Patent Documents 4 and 5), a composition for hair treatment containing a copolymer obtained from solution polymerization of an ingredient of ethylene unsaturated monomer (for example, see Patent Document 6), and a hair holding formulation using a combination of specific polymers (for example, see Patent Document 7).

In addition, particularly an oxidation type, two-agent type bleaching or hair dye composition among a bleaching or hair dye composition, causes hair damage, and produces hair entanglement or bad touch at the time of water washing or shampoo washing. Further, this hair entanglement becomes a cause for gloss loss of hair after finish and bad manageability. In addition, hair after hair dyeing is further under damage by heat from, for example, a drier, a hair iron, or physical stimulation from routine hair care action such as brushing. For this reason, there are problems that the touch becomes further worse from hair entanglement at the time of water washing or shampoo washing, and gloss or manageability of hair after finish further decrease.

Accordingly, in order to improve effects such as touch at the time of wetting or after drying, persistence thereof, and color sustention, proposed is a technique of rendering a specific cationic polymer to coexist together with amino-modified silicone and high molecular weight silicone to improve the adsorbed amount of silicones (Patent Document 8).

Meanwhile, proposed is a bleaching or hair dye composition containing an amphoteric or cationic polymer and an anionic polymer in combination, which improves gloss and flexibility of hair, and allows further natural dyed color and sufficient fastness properties (Patent Document 9).

In addition, proposed is a conditioning composition containing a cationic surfactant and an anionic or amphoteric polymer, and further a cationic polymer as an optional ingredient (Patent Document 10). In this Document, examples of the preferred anionic polymer include carboxymethyl celluloses having a viscosity of about 5,000 to about 10,000 mPa·s and a substitution degree of about 0.5 to about 0.8 in 1% aqueous solution (paragraph [0051]), and examples of the preferred a cationic polymer include a dimethyldiallyl ammonium chloride homopolymer, and a copolymer of acrylamide and dimethyldiallyl ammonium chloride (paragraph [0079]).

Patent Document 1 JP 2004-323423 A
Patent Document 2 JP 2008-543949 W
Patent Document 3 JP 2006-282674 A
Patent Document 4 JP 2005-36014 A
Patent Document 5 JP H10-95714 A
Patent Document 6 JP 2012-136464 A
Patent Document 7 JP 2009-504661 W
Patent Document 8 JP 2008-290953 A
Patent Document 9 JP 2002-193772 A
Patent Document 10 JP 2008-546806 W

SUMMARY OF THE INVENTION

The inventors have found that the problems can be solved all at once by a hair cosmetic comprising a specific cationic polymer and a specific anionic polysaccharide derivative.

The invention provides a hair cosmetic comprising the following ingredients (A) and (B):

(A) a cationic polymer having a charge density of 5.0 meq/g or more and 7.0 meq/g or less and (B) an anionic polysaccharide derivative wherein a part of the hydrogen atoms of the hydroxyl group of a polysaccharide compound having a constituent unit represented by the formula (1) are substituted with —$(CH_2)_m COO^-$ groups (m is an integer of 1 to 5) at an average substitution degree of 0.5 or more and 2.0 or less per constituent unit, and wherein optionally a part of the hydrogen atoms of the remaining hydroxyl groups are substituted with linear or branched $C_{1-40}$ alkyl groups and/or alkylene groups, wherein the viscosity of the ingredient (B) in a 2 mass % aqueous solution at 25° C. is 0.5 mPa·s or more and 800 mPa·s or less:

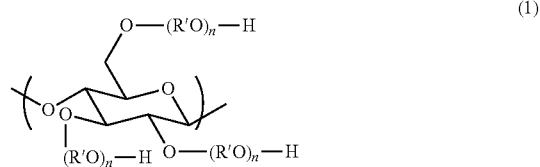

(1)

wherein R' may be the same or different, and represents a $C_{2-4}$ linear or branched alkylene group optionally substituted with a hydroxyl group, and n represents a number by which the average number of added moles of R'O per constituent unit is 0 to 10.

DETAILED DESCRIPTION OF THE INVENTION

With any technique of Patent Documents 4 to 7, the effect of improving the appearance and the touch of damaged hair to those of healthy hair is insufficient, and particularly the effect of improving finger-combing smoothness of wet hair is not considered. In addition, although addition of conditioning ingredients to a two-agent type bleaching or hair dye composition was performed, a majority of the additives was washed away by hair-washing or rinsing after the treatment and only a small amount remained on hair, and thus such effects were not sufficiently satisfactory. Further, with the technique of Patent Document 8, persistence of the effects is limited, and is not sufficiently satisfactory. In addition, persistence of the effects is not described at all in Patent Documents 9 and 10.

The invention relates to a hair cosmetic that can improve touch and appearance of damaged hair to like those of healthy hair, and especially improve finger-combing smoothness and combability of wet hair and manageability and gloss of dry hair, and retain such effects without being impaired by repetitive hair washings.

When the hair cosmetic is a bleaching or hair dye composition, in the specification, a first agent refers to a composition containing an alkali agent, a second agent refers to a composition containing hydrogen peroxide, and a third agent refers to a composition containing other active ingredients excluding the alkali agent and the hydrogen peroxide. Further, a content of each ingredient "in a bleaching or hair dye composition" refers to a content "in the bleaching or hair dye composition" in a case of a one-agent type; refers to a content "in a mixture of the first agent and the second agent" in a case of a two-agent type; and refers to a content "in a mixture comprising the first agent to the third agent" in a case of a three-agent type.

<Ingredient (A): Cationic Polymer Having Charge Density of 5.0 Meq/g or More and 7.0 Meq/g or Less>

The hair cosmetic of the invention contains a cationic polymer having a charge density of 5.0 meq/g or more and 7.0 meq/g or less. Herein, the charge density in the cationic polymer refers to moles of cationic group×1000 (meq/g) per 1 g of polymer.

The charge density of the ingredient (A) is preferably 5.2 meq/g or more, more preferably 5.5 meq/g or more, further preferably 5.8 meq/g or more and further preferably 6.0 meq/g from the viewpoint of persistence of finger-combing smoothness of wet hair and persistence of manageability of dry hair, and is preferably 6.5 meq/g or less from the viewpoint of obtaining good touch of hair.

Examples of the ingredient (A) include a polymer comprising a diallyl quaternary ammonium salt as a constituent unit and a quaternized polyvinyl imidazolium derivative.

The polymer comprising a diallyl quaternary ammonium salt as a constituent unit is preferably those having a backbone represented by the following formula (2) or (3):

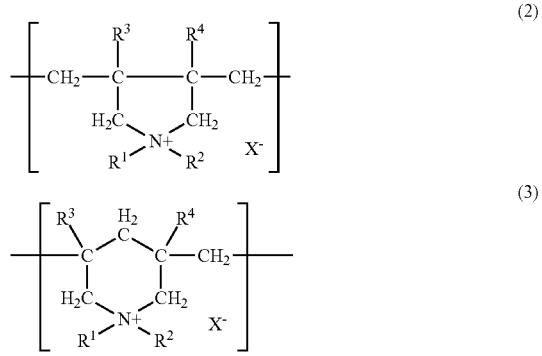

wherein $R^1$ and $R^2$ may be the same or different, and represents a hydrogen atom, a $C_{1-18}$ alkyl group, an aryl group (such as phenyl group), a hydroxyalkyl group, an amidoalkyl group, a cyanoalkyl group, an alkoxyalkyl group or a carboalkoxyalkyl group; $R^3$ and $R^4$ may be the same or different, and represents a hydrogen atom, a $C_{1-3}$ alkyl group or a phenyl group; and $X^-$ represents an anion (for example, a chloride ion, a bromide ion, an iodide ion, a sulfate anion, a sulfonate anion, a methylsulfate anion, a phosphate anion, and a nitrate anion).

The polymer of a diallyl quaternary ammonium salt contains the constituent unit represented by the formula (2) or (3) preferably by 65 to 100 mol %, more preferably by 75 to 100 mol %, further preferably by 90 to 100 mol %, and further preferably by 95 to 100 mol % in one molecule from the viewpoint of persistence of finger-combing smoothness and combability of wet hair, and persistence of manageability and glossy feeling of dry hair.

Specific examples of the polymer comprising a diallyl quaternary ammonium salt as a constituent unit include those represented by the following formula (4) or (5):

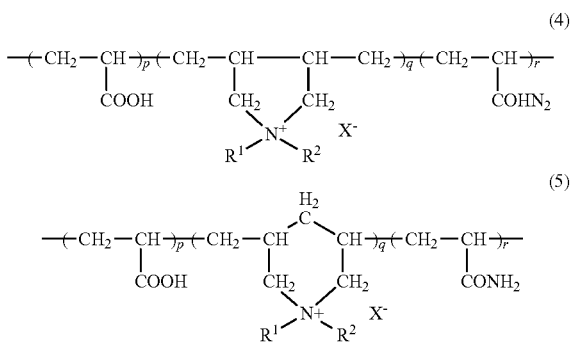

wherein $R^1$, $R^2$ and $X^-$ are defined as above. p, q and r represent molar ratios, and p+q+r=100.

p is preferably 0 to 50, more preferably 0 to 25, further preferably 0 to 10 and further preferably 0 to 5, q is preferably 50 to 100, more preferably 65 to 100, further preferably 75 to 100, further preferably 90 to 100 and further preferably 95 to 100, and r is preferably 0 to 50, more preferably 0 to 25, further preferably 0 to 10 and further preferably 0 to 5.

Among them, the polymer comprising a diallyl quaternary ammonium salt as a constituent unit is preferably a homopolymer of a diallyl quaternary ammonium salt or a copolymer of a diallyl quaternary ammonium salt and an acrylic acid. Specific examples of the homopolymer of a diallyl quaternary ammonium salt include Merquat 100 (having 6.2 meq/g of the charge density and 150,000 of the weight average molecular weight manufactured by Lubrizol Advanced Materials, Inc.). Specific examples of the copolymer of a diallyl quaternary ammonium salt and an acrylic acid include Merquat 295 (having 6.0 meq/g of the charge density and 190,000 of the weight average molecular weight manufactured by Lubrizol Advanced Materials, Inc.) and Merquat 280 (having 5.0 meq/g of the charge density and 450,000 of the weight average molecular weight manufactured by Lubrizol Advanced Materials, Inc.).

The quaternized polyvinyl imidazolium derivative is preferably, for example, those represented by the following formula (6):

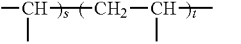

wherein R represents a hydrogen atom or a $C_{1-3}$ alkyl group, Y represents an anion such as a chloride ion, a bromide ion, an iodide ion, a sulfate anion, a sulfonate anion, a $C_{1-4}$ alkyl sulfate anion, a phosphate anion and a nitrate anion, s and t represent molar ratios and s+t=100.

The molar ratio t of the monomer having cationic property is preferably 73 or more, more preferably 90 or more and further preferably 93 or more, and preferably 99 or less from the viewpoint of persistence of finger-combing smoothness and combability of wet hair, and persistence of manageability and glossy feeling of dry hair.

Specific examples of such quaternized polyvinyl imidazolium derivative include a copolymer of vinyl pyrrolidone and methylvinyl imidazolium chloride (Luviquat Excellence (having 6.1 meq/g of the charge density and 40,000 of the weight average molecular weight, manufactured by BASF)).

The weight average molecular weight of the ingredient (A) is preferably 10,000 or more, more preferably 50,000 or more and further preferably 100,000 or more from the viewpoint of persistence of finger-combing smoothness and combability of wet hair, and persistence of manageability and glossy feeling of dry hair, and is preferably 3,000,000 or less, more preferably 1,000,000 or less and further preferably 800,000 or less from the viewpoint of obtaining good touch.

Herein, the weight average molecular weight can be measured, for example, under the conditions below by gel permeation chromatography (GPC).

Mobile phase: 50 mM LiBr, 1% $CH_3COOH$/ethanol: water=3:7

Column: TSK gel α-M (two in series)

Reference material: polyethylene glycol

Among these ingredients (A), the ingredient (A) is preferably a homopolymer of a diallyl quaternary ammonium salt, or a copolymer of a diallyl quaternary ammonium salt and an acrylic acid.

When the hair cosmetic is a two-agent type or three-agent type bleaching or hair dye composition, the ingredient (A) may be contained in any one of the first agent, the second agent and the third agent.

The content of the ingredient (A) in the hair cosmetic is preferably 0.01 mass % or more, more preferably 0.1 mass % or more, further preferably 0.5 mass % or more and further preferably 0.75 mass % or more, and is preferably 20 mass % or less, more preferably 10 mass % or less, further preferably 5 mass % or less, further preferably 3 mass % or less, further preferably 2.5 mass % or less and further preferably 2 mass % or less from the viewpoint of persistence of finger-combing smoothness and combability of wet hair, and persistence of manageability and glossy feeling of dry hair.

<Ingredient (B) Anionic Polysaccharide Derivative>

The hair cosmetic of the invention contains an anionic polysaccharide derivative wherein a part of the hydrogen atoms of the hydroxyl group of a polysaccharide compound having a constituent unit represented by the formula (1) are substituted with —$(CH_2)_mCOO^-$ groups (m is an integer of 1 to 5) at an average substitution degree of 0.5 or more and 2.0 or less per constituent unit, and wherein optionally a part of the hydrogen atoms of the remaining hydroxyl groups are substituted with linear or branched $C_{1-40}$ alkyl groups and/or alkylene groups, wherein the viscosity of the ingredient (B) in a 2 mass % aqueous solution at 25° C. is 0.5 mPa·s or more and 800 mPa·s or less:

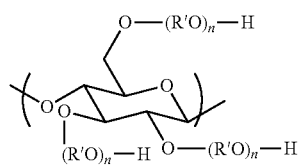

(1)

wherein R' may be the same or different, and represents a $C_{2-4}$ linear or branched alkylene group optionally substituted with a hydroxyl group, and n represents a number by which the average number of added moles of R'O per constituent unit is 0 to 10.

As the polysaccharide compound having a constituent unit represented by the formula (1), at least one member selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum and hydroxypropylmethyl starch can be suitably used. Among them, cellulose and hydroxyethyl cellulose can be further suitably used.

[Viscosity of 2 Mass % Aqueous Solution]

The viscosity of the ingredient (B) in a 2 mass % aqueous solution at 25° C. is preferably 1 mPa·s or more, and more preferably 2 mPa·s or more from the viewpoint of persistence of finger-combing smoothness and combability of wet hair, and persistence of manageability and glossy feeling of dry hair, and is preferably 500 mPa·s or less, more preferably 300 mPa·s or less, further preferably 150 mPa·s or less, further preferably 120 mPa·s or less, further preferably 100 mPa·s or less, further preferably 50 mPa·s or less, and further preferably 20 mPa·s or less from the viewpoint of obtaining good touch. Meanwhile, the viscosity of the ingredient (B) in the invention is measured in accordance with the method described below.

Method for Measuring Viscosity of 2 Mass % Aqueous Solution (mPa·s)

About 4.8 g of an anionic polysaccharide derivative having a known moisture value is precisely weighed in a 300 mL stoppered Erlenmeyer flask, and the flask is added with 200 g of distilled water, and immediately capped and strongly vibrated to disperse the anionic polysaccharide derivative to small lumps, and left to stand. The resultant is left overnight (about 18 to 20 hours), and then matched to 2 mass % aqueous solution concentration with correction water from the known moisture value. The amount of correction water is calculated based on the calculation formula below from the separately determined moisture.

Amount of correction water (g)=Anionic polysaccharide derivative sample (g)×{(98−moisture content of sample (%))/2}−200

After completion of the correction, a small stirring bar is put into the Erlenmeyer flask, and the mixture is stirred for 25 minutes with a magnetic stirrer, to completely disperse and dissolve the swollen content. Subsequently, this solution is moved to a 250 mL volume container with a plug (50 mm diameter×140 mm height), and the container is capped and left to stand for 30 minutes in a thermostat bath at 25° C. After confirming the temperature as 25° C., this container with a plug is installed with a BM type viscometer, a rotor and a guard, and the scale after 3 minutes is read. At this time, the rotor No. is selected in accordance with the expected viscosity, and the number of revolution is set to 60 rpm.

[Average Substitution Degree]

The average substitution degree per constituent unit of the group —$(CH_2)_mCOO^-$ in the ingredient (B) is preferably 0.6 or more and more preferably 0.65 or more from the viewpoint of persistence of finger-combing smoothness and combability of wet hair, and persistence of manageability and glossy feeling of dry hair, and is preferably 1.5 or less, more preferably 1.2 or less and further preferably 0.9 or less from the viewpoint of the touch. Meanwhile, the average substitution degree in the invention is measured in accordance with the method described below.

Method for Measuring Average Substitution Degree

A Method for measuring the average substitution degree is explained with reference to an example where the introduced substituent is —$(CH_2)_m$COONa.

A bone-dried anionic polysaccharide derivative is wet-decomposed with sulfuric acid-hydrogen peroxide using a microwave wet-type ashing apparatus (trade name: "A-300" manufactured by PROLABO), and then the Na content (%) is measured with an atom absorption method using an atom absorption device (trade name: "Z-6100 type" manufactured by Hitachi, Ltd.), and the substitution degree is calculated from the calculation formula described below.

$$\text{Average substitution degree (DS)} = (x \times \text{Na content (\%)})/(2300 - y \times \text{Na content (\%)})$$

x: Average molecular weight per one unit of sugar monomer consisting of polysaccharide derivative before introduction of anionic substituent y: Increment of molecular weight by introduction of one substituent Specific examples of the ingredient (B) include CELLOGENs F-5A, F-7A, F-907A, F-815A, F-SB and F-930A (carboxymethyl cellulose manufactured by DKS Co. Ltd.), San Roses F-01MC, FT-1, F04HC and APP-84 (carboxymethyl cellulose manufactured by Nippon Paper Industries Co., Ltd.), CMC Daicels 1105, 1110, 1130, 1205, 1210, 1220, 1230, 1240, 1250 and 1330 (carboxymethyl cellulose manufactured by Daicel Corporation), and Blanoses 7LF, 7M1F, 7MF, 7M8SF and 12M8P (carboxymethyl cellulose manufactured by ISP Ltd).

When the hair cosmetic is a bleaching or hair dye composition, the ingredient (B) is preferably contained in the first agent when the hair cosmetic is of a two-agent type, and is preferably contained in the first agent or the third agent, and more preferably contained in the third agent when the hair cosmetic is of a three-agent type from the viewpoint of stability.

The content of the ingredient (B) in the hair cosmetic is preferably 0.01 mass % or more, more preferably 0.1 mass % or more, further preferably 0.3 mass % or more and further preferably 0.5 mass % or more, and is preferably 20 mass % or less, more preferably 10 mass % or less, further preferably 5 mass % or less, further preferably 3 mass % or less, further preferably 2 mass % or less and further preferably 1.5 mass % or less from the viewpoint of persistence of finger-combing smoothness and combability of wet hair, and persistence of manageability and glossy feeling of dry hair.

The mass ratio of the ingredient (A) to the ingredient (B), (A)/(B) in the hair cosmetic in the invention is preferably 0.1 or more, more preferably 0.2 or more, further preferably 0.3 or more and further preferably 0.5 or more, and is preferably 30 or less, more preferably 15 or less, further preferably 10 or less, further preferably 5 or less, further preferably 3 or less, further preferably 2 or less and further preferably 1.5 or less from the viewpoint of persistence of finger-combing smoothness and combability of wet hair, and persistence of manageability and glossy feeling of dry hair.

When the hair cosmetic is a two-agent type or three-agent type bleaching or hair dye composition, the ingredient (A) and the ingredient (B) are preferably contained in different agents from the viewpoint of stability. When the hair cosmetic is of a two-agent type, the ingredient (B) is preferably contained in the first agent and the ingredient (A) in the second agent, and when the hair cosmetic is of a three-agent type, the ingredient (B) is preferably contained in the first agent or the third agent, and the ingredient (A) in the second agent.

[Surfactant]

A surfactant may be contained in the hair cosmetic of the invention. When the hair cosmetic is a two-agent type or three-agent type bleaching or hair dye composition, a surfactant may be contained in any one of the first agent, the second agent and the third agent. As the surfactant, any one of an anionic surfactant, a nonionic surfactant, a cationic surfactant and an amphoteric surfactant can be used.

Examples of the anionic surfactant include, for example, a sulfuric acid ester-based anionic surfactant such as alkyl sulfate and alkyl ether sulfate; a carboxylic acid-based anionic surfactant such as an N-acylamino acid salt, an N-acyl-N-alkyl amino acid salt, an amide type N-acylamino acid salt, an ether carboxylate, a fatty acid salt, an alkyl succinate and an alkenyl succinate; a sulfonic acid-based anionic surfactant such as a sulfosuccinate type, an isethionate type, a taurinate type, an alkyl benzenesulfonate type, an α-olefin sulfonate type and an alkane sulfonic acid type; and a phosphoric acid ester-based anionic surfactant such as an alkyl phosphate and an alkyl ether phosphate. Among them, the anionic surfactant is preferably a carboxylic acid-based or sulfuric acid ester-based anionic surfactant, and most especially preferably a carboxylic acid-based anionic surfactant. Among the carboxylic acid-based anionic surfactant, the anionic surfactant is preferably an N-acylamino acid salt or ether carboxylate. Among them, the anionic surfactant is preferably an N-acyl glutamic acid salt having a carbon number of 10 to 18, preferably 10 to 16 and further preferably 10 to 14 in the acyl group, or polyoxyethylene alkyl carboxylate having a carbon number of 10 to 18, preferably 10 to 16 and further preferably 10 to 14 in the alkyl group and having an average number of added moles of the oxyethylene groups of 3 to 15, preferably 3 to 12 and further preferably 4 to 10.

Examples of the nonionic surfactant include an alkyl polyglucoside, a polyoxyalkylene alkyl ether, and an alkylglyceryl ether. The alkyl polyglucoside is preferably those having a carbon number of 8 to 18, further 8 to 14 and further 9 to 11 in the alkyl group, wherein this alkyl group is preferably linear. The average polymerization degree of the glucoside is preferably 1 to 5, and further preferably 1 to 2. The polyoxyalkylene alkyl ether is preferably those having a carbon number of 10 to 22 and further 12 to 18 in the alkyl group, wherein this alkyl group is preferably linear. In addition, the nonionic surfactant is more preferably a polyoxyethylene alkyl ether, and most especially preferably those having 1 to 50, and further 2 to 40 of the average number of added moles of the oxyethylene groups. The alkyl glyceryl ether is preferably those having a carbon number of 8 to 18 and further 8 to 12 in the alkyl group, wherein this alkyl group is preferably branched.

The cationic surfactant is preferably a mono-long chain alkyl quaternary ammonium salt or di-long chain alkyl quaternary ammonium salt, and examples thereof include specifically cetrimonium chloride, steartrimonium chloride, behentrimonium chloride, stearalkonium chloride, benzalkonium chloride, stearoxypropyl trimonium chloride, and dialkyl ($C_{12-18}$) dimonium chloride, and the cationic surfactant is more preferably steartrimonium chloride, behentrimonium chloride, stearoxypropyl trimonium chloride or dialkyl ($C_{12-18}$) dimonium chloride. Examples of a commercial product of the cationic surfactant include QUARTAMINs 86W, 86P CONC, 60W, E-80K and D2345P (manufactured by Kao Corporation), and Nikkol CA-2580 (manufactured by Nihon Surfactant Kogyo K.K.).

Examples of the amphoteric surfactant include carbonbetaine-based, amidobetaine-based, sulfobetaine-based, hydroxysulfobetaine-based, amidosulfobetaine-based, phosphobetaine-based, and imidazolinium based surfactant having a $C_{8-24}$ alkyl group, alkenyl group or acyl group, and the amphoteric surfactant is preferably a carbonbetaine-based surfactant and a sulfobetaine-based surfactant having a $C_{8-24}$ alkyl group, alkenyl group or acyl group. Examples of a preferred amphoteric surfactant include lauric acid amidopropyl betaine, coconut oil fatty acid amidopropyl betaine, lauryldimethylaminoacetic acid betaine, and lauryl hydroxysulfobetaine.

The surfactant may be combined in 2 or more members, and the content in the hair cosmetic is preferably 0.1 mass % or more, more preferably 0.5 mass % or more and further preferably 1 mass % or more, and is preferably 30 mass % or less, more preferably 25 mass % or less, further preferably 20 mass % or less and further preferably 15 mass % or less from the viewpoint of the stability of the hair cosmetic.

When the hair cosmetic of the invention is a shampoo, the hair cosmetic of the invention preferably contains an anionic surfactant. A sulfuric acid ester-based anionic surfactant such as alkyl sulfate and alkyl ether sulfate is suitably used among them from the viewpoint of foaming and washability. The content of the anionic surfactant in a shampoo is preferably 2 mass % or more, further 2.5 mass % or more, further 3 mass % or more and further 5 mass % or more, and is preferably 30 mass % or less, further 25 mass % or less, further 20 mass % or less and further 15 mass % or less. The mass ratio of the anionic surfactant to the sum of the ingredient (A) and the ingredient (B) (anionic surfactant/[ingredient (A)+ingredient (B)]) is preferably 0.3 or more, further 0.5 or more, further 1 or more and further 1.5 or more, and is preferably 10 or less, further 8 or less, further 7 or less and further 4 or less from the viewpoint of the stability of a shampoo.

In addition, when the hair cosmetic of the invention is a hair rinse, a hair conditioner or a hair treatment, the hair cosmetic of the invention preferably contains a cationic surfactant. The cationic surfactant is preferably a mono-long chain alkyl quaternary ammonium salt or a di-long chain alkyl quaternary ammonium salt among them from the viewpoint of smoothening of hair after rinsing or drying. The content of the cationic surfactant in a hair rinse, hair conditioner or hair treatment is preferably 0.1 mass % or more, further 0.5 mass % or more and further 1 mass % or more, and is preferably 15 mass % or less, further 10 mass % or less and further 8 mass % or less. The mass ratio of the cationic surfactant to the sum of the ingredient (A) and the ingredient (B) (cationic surfactant/[ingredient (A)+ingredient (B)]) is preferably 0.3 or more, further 0.5 or more and further 1 or more, and is preferably 10 or less, further 8 or less, further 6 or less, further 4 or less and further 2 or less from the viewpoint of the stability of the hair rinse, the hair conditioner or the hair treatment.

In addition, when the hair cosmetic of the invention is a bleaching or hair dye composition, the content of the surfactant is preferably 2 mass % or more, further 2.5 mass % or more and further 3 mass % or more, and is preferably 20 mass % or less, further 15 mass % or less, further 10 mass % or less, further 8 mass % or less, further 7 mass % or less and further 6 mass % or less from the viewpoint of the stability of the bleaching or hair dye composition.

[Higher Alcohol]

A higher alcohol having a carbon number of 12 or more is preferably contained in the hair cosmetic of the invention from the viewpoint of improvement of touch and stability. They have effects of forming a structure with a surfactant to prevent separation, and improving the touch at the time of rinsing. When the hair cosmetic is a two-agent type or three-agent type bleaching agent or hair dye composition, higher alcohol may be contained in any one of the first agent, the second agent and the third agent the agent.

The higher alcohol is preferably those having a carbon number of 12 or more and further 16 or more, and 30 or less and further 22 or less, and examples thereof include specifically myristyl alcohol, cetyl alcohol, stearyl alcohol, arachyl alcohol, behenyl alcohol, isostearyl alcohol, 2-octyl dodecanol, oleyl alcohol, and a mixture thereof.

The higher alcohol may be combined in 2 or more members, and the content thereof is preferably 3 mass % or more and further 4 mass % or more, and is preferably 11 mass % or less and further 9 mass % or less in the hair cosmetic from the viewpoint of the viscosity and the stability of the hair cosmetic.

[Polyhydric Alcohol]

The hair cosmetic of the invention preferably further contains a polyhydric alcohol. When the hair cosmetic is a two-agent type or three-agent type bleaching agent or hair dye composition, the polyhydric alcohol may be contained in any one of the first agent, the second agent and the third agent. Examples of the polyhydric alcohol include those of $C_{2-20}$, specifically alkylene glycols such as ethylene glycol, diethylene glycol, triethylene glycol, polyethylene glycol, propylene glycol, dipropylene glycol, polypropylene glycol, 1,2-butylene glycol, 1,3-butylene glycol, pentylene glycol and hexylene glycol; glycerins such as glycerin, diglycerin and polyglycerin; sugar alcohols such as xylitol, mannitol, galactitol and sorbitol; and in addition, trimethylol ethane, trimethylol propane, and pentaerythritol.

The polyhydric alcohol may be combined in 2 or more members. In addition, the content in the hair cosmetic is preferably 0.1 mass % or more, further 0.5 mass % or more and further 1 mass % or more, and is preferably 20 mass % or less, further 15 mass % or less and further 10 mass % or less from the point of excellent effects of giving moisture to hair and suppressing loose feeling of hair.

[Conditioning Ingredient]

In addition, the hair cosmetic of the invention may contain a conditioning ingredient selected from silicones and oils.

Examples of the silicones include, for example, polydimethyl siloxanes, modified silicones (for example, amino-modified silicone, fluorine-modified silicone, alcohol-modified silicone, polyether-modified silicone, epoxy-modified silicone, alkyl-modified silicone, aminopolyether-modified silicone), cyclic polydimethyl siloxanes and high molecular weight methylpolysiloxane emulsions, and particularly the silicones are preferably polydimethyl siloxanes, polyether-modified silicones, amino-modified silicones, cyclic polydimethyl siloxanes, aminopolyether-modified silicones or high molecular weight methylpolysiloxane emulsions.

These silicones can be used alone or in combination of 2 or more members. The content of silicones is preferably 0.1 mass % or more and further 0.5 mass % or more in the hair cosmetic from the viewpoint of sufficient effects, and is preferably 20 mass % or less and further 15 mass % or less in the hair cosmetic from the viewpoint of suppressing stickiness.

Examples of the oil include a hydrocarbon such as squalene, squalane, Vaseline, paraffin, liquid paraffin, liquid isoparaffin and cycloparaffin; a glyceride such as castor oil, cacao-seed oil, mink oil, avocado oil, olive oil and shea fat; a wax such as bees wax, whale wax, lanolin and carnauba wax; ester oil such as isopropyl palmitate, isopropyl myristate, octyldodecyl myristate, hexyl laurate, cetyl lactate, propylene glycol monostearate, oleyl oleate, hexadecyl 2-ethyl hexanoate, isononyl isononanate and tridecyl isononanate; a higher fatty acid such as capric acid, lauric acid, myristic acid, palmitic acid, stearic acid, behenic acid, oleic acid, lanolin fatty acid, isofatty acid, anteiso-fatty acid, coconut oil fatty acid, 18-methyleicosanoic acid and 16-methyloctadecanoic acid and a mixture of these fatty acids/branched fatty acids.

These oils can be used alone or in combination of 2 or more members. The content of the oil is preferably 0.1 mass % or more and further 0.5 mass % or more in the hair cosmetic from the viewpoint of the effect of improving the touch, and is preferably 20 mass % or less and further 15 mass % or less in the hair cosmetic from the viewpoint of stability against separation of the hair cosmetic.

By such conditioning ingredient moderately remaining on hair, it is possible to give good conditioning effect.

[Dye]

When the hair cosmetic of the invention is a hair dye composition, the hair cosmetic of the invention contains a dye. When the hair dye composition is of one-agent type, the hair dye composition may contain a direct dye, and when the hair dye composition is of two-agent type or three-agent type, the hair dye composition may contain an oxidation dye intermediate or a direct dye in the first agent.

(Oxidation Dye Intermediate)

As the oxidation dye intermediate, a known precursor and coupler ordinarily used in a hair dye may be used. Examples of the precursor include, p-phenylene diamine, toluene-2,5-diamine, N-phenyl p-phenylene diamine, N,N-bis(hydroxyethyl) p-phenylene diamine, 2-hydroxyethyl p-phenylene diamine, para-aminophenol, para-methylaminophenol, 4-amino-metacresol, ortho-aminophenol, and a salt thereof.

Examples of the coupler include, resorcin, 2-methylresorcin, 1-naphthol, 1,5-dihydroxynaphthalene, 5-aminoorthocresol, metha-phenylene diamine, metha-aminophenol, 2,4-diaminophenoxyethanol, 2,6-diaminopyridine, 2-methyl-5-hydroxyethyl aminophenol, 2-amino-3-hydroxypyridine, and a salt thereof.

The precursor and the coupler may be combined in 2 or more members, respectively, and respective content of the precursor and the coupler is preferably 0.01 mass % or more and further 0.1 mass % or more, and is preferably 5 mass % or less and further 4 mass % or less in the hair dye composition.

(Direct Dye)

Examples of the direct dye include an acidic dye, a nitro dye, a dispersed dye, and a basic dye. More specifically, examples of the acidic dye include Blue No. 1, Violet No. 401, Black No. 401, Orange No. 205, Red No. 227, Red No. 106, Yellow No. 203, and Acidic Orange No. 3; examples of the nitro dye include 2-nitro-p-phenylene diamine, 2-amino-6-chloro-4-nitro phenol, 3-nitro-p-hydroxyethyl aminophenol, 4-nitro-o-phenylene diamine, 4-amino-3-nitro phenol, 4-hydroxypropyl amino-3-nitro phenol, HC Blue 2, HC Orange No. 1, HC Red 1, HC Yellow 2, HC Yellow 4, HC Yellow 5, HC Red 3, and N,N-bis(2-hydroxyethyl)-2-nitro-p-phenylene diamine; examples of the dispersed dye include Dispersed Violet 1, Dispersed Blue 1, and Dispersed Black 9; and examples of the basic dye include Basic Blue 99, Basic Brown 16, Basic Brown 17, Basic Red 76, Basic Yellow 76, Basic Orange No. 31, and Basic Red 51.

Two members or more of the direct dye may be used in combination, and when the hair dye composition is a two-agent type or three-agent type, the direct dye may be combined with an oxidation dye intermediate. In addition, the content thereof is preferably 0.001 mass % or more and further 0.01 mass % or more, and is preferably 5 mass % or less and further 3 mass % or less in the hair dye composition.

[Alkali Agent]

When the hair cosmetic of the invention is a bleaching or hair dye composition, an alkali agent may be contained. When the bleaching or hair dye composition is of two-agent type or three-agent type, the alkali agent is contained in the first agent. Examples of the alkali agent include ammonia and a salt thereof, sodium hydroxide, potassium hydroxide, an alkanol amine such as monoethanol amine, isopropanol amine, 2-amino-2-methylpropanol and 2-aminobutanol and a salt thereof, an alkane diamine such as 1,3-propanediamine and a salt thereof, and a carbonate such as sodium carbonate, potassium carbonate, sodium bicarbonate, potassium bicarbonate, and guanidine carbonate.

Two members or more of the alkali agent may be used in combination, and the content in the bleaching or hair dye composition is preferably 0.05 mass % or more, further 0.1 mass % or more and further 0.2 mass % or more from the point of sufficient hair dyeing effect, and is preferably 5 mass % or less and further 4 mass % or less from the point of decrease of hair damage and scalp stimulation.

[Hydrogen Peroxide]

When the bleaching or hair dye composition of the invention is of two-agent type or three-agent type, hydrogen peroxide may be contained in the second agent. The content of hydrogen peroxide in the bleaching or hair dye composition is preferably 0.1 mass % or more, further 0.5 mass % or more and further 1 mass % or more from the point of sufficient hair dyeing effect, and is preferably 12 mass % or less, further 9 mass % or less and further 6 mass % or less from the point of decreasing hair damage and scalp stimulation.

[Other Optional Ingredient]

Other ingredients ordinarily used as a cosmetic raw material can be added in addition to the ingredients described above in the hair cosmetic of the invention. Examples of such optional ingredient include a thickener, a preservative, a chelating agent, a stabilizer, an antioxidant, a vegetable extract, a galenical extract, a protein hydrolyzate, vitamins, a colorant such as a dye, a flavor, an ultraviolet absorber, a pearl ingredient such as ethylene glycol difatty acid ester, a polymer for setting, and amphipathic amide lipid.

Examples of the polymer for setting include polysilicone-9; a polyvinyl pyrrolidone-based polymer (for example, polyvinyl pyrrolidone, a copolymer of vinyl pyrrolidone/vinyl acetate, a ternary copolymer of vinyl pyrrolidone/vinyl acetate/vinyl propionate, a copolymer of vinyl pyrrolidone/alkyl aminoacrylate (quaternary chloride), a copolymer of vinyl pyrrolidone/acrylate/(meth)acrylic acid, a copolymer of vinyl pyrrolidone/alkyl aminoacrylate/vinyl caprolactam); a copolymer of methylvinyl ether/maleic anhydride alkyl half ester; an acidic polyvinyl acetate-based polymer (for example, a copolymer of a vinyl acetate/crotonic acid, a copolymer of vinyl acetate/crotonic acid/vinyl neodecanoate, a copolymer vinyl acetate/crotonic acid/vinyl propionate); an acidic (meth)acrylic polymer (for example, a copolymer of (meth)acrylic acid/(meth)acrylic acid ester, a copolymer of acrylic acid/acrylic acid alkyl ester/alkyl acrylamide); an amphoteric acrylic polymer (for example, a copolymer of N-methacryloylethyl-N,N-dimethylammonium•α-N-methylcarboxybetaine/butyl methacrylate, a copolymer of hydroxypropyl acrylate/aminoethylbutyl methacrylate/octyl acrylate amide); an acrylamide•acrylic acid ester-based copolymer; and a chitin•chitosan compound (for example, hydroxypropyl chitosan, carboxymethyl chitin, carboxymethyl chitosan).

The content of the polymer for setting in the hair cosmetic is preferably 0.1 mass % or more and further 0.5 mass % or more, and is preferably 5 mass % or less and further 3 mass % or less. The polymer for setting is further suitably used when the hair cosmetic is a styling agent.

[Medium]

Water is used as a medium in the hair cosmetic of the invention. The content of water in the hair cosmetic is preferably 10 mass % or more, further 20 mass % or more and further 30 mass % or more, and is preferably 90 mass % or less, further 80 mass % or less and further 75 mass % or less.

An organic solvent may be further used as another medium than water as necessary in the hair cosmetic of the invention. Examples of the organic solvent include aromatic alcohols such as benzyl alcohol and benzyloxyethanol, lower alkanols such as ethanol and 2-propanol, polyols such as propylene glycol, 1,3-butanediol, diethylene glycol and glycerin, cellosolves such as ethyl cellosolve, butyl cellosolve and benzyl cellosolve, and carbitols such as ethyl carbitol and butyl carbitol.

[pH]

When the hair cosmetic of the invention is not a bleaching agent or hair dye composition, the pH of the hair cosmetic at 25° C. is preferably 2 or more, more preferably 4.5 or more and further preferably 5.5 or more, and is preferably 12 or less, more preferably 11.5 or less and further preferably 11 or less.

When the hair cosmetic of the invention is a bleaching agent or hair dye composition, a preferred pH of the bleaching agent or hair dye composition at 25° C. is as described below. The pH of the bleaching agent or hair dye composition at 25° C. is preferably 1 or more and further 2.5 or more, and is preferably 5.5 or less and further 4.5 or less in a case of a one-agent type hair dyeing composition using an acidic dye. In addition, in a case of a one-agent type hair dyeing composition using a basic dye, the pH of the bleaching agent or hair dye composition at 25° C. is preferably 3.5 or more and further 4 or more, and is preferably 8 or less and further 6 or less. In addition, in a case of a two-agent type or three-agent type bleaching agent or hair dye composition, pH of the first agent (25° C.) is preferably 8 to 12, and the pH of the second agent (25° C.) is preferably 2 to 5, and the pH of a mixture of the first agent and the second agent or the pH of a mixture of the first agent, the second agent and the third agent (25° C.) is preferably 8 to 11.5 and further 9 to 11 from the point of bleaching and hair dyeing effects and skin stimulation.

A pH regulating agent can be used in order to regulate the pH. As the pH regulating agent, use can be made of ammonia or a salt thereof; an alkanol amine such as monoethanol amine, isopropanol amine, 2-amino-2-methyl-propanol and 2-aminobutanol or a salt thereof; an alkane diamine such as 1,3-propanediamine or a salt thereof; a carbonate such as guanidine carbonate, sodium carbonate, potassium carbonate, sodium bicarbonate and potassium bicarbonate; and a hydroxide such as sodium hydroxide and potassium hydroxide, as an alkali agent. In addition, use can be made of an inorganic acid such as hydrochloric acid and phosphoric acid; an organic acid such as citric acid, glycolic acid and lactic acid; a hydrochloride such as monoethanolamine hydrochloride; and a phosphate such as monopotassium dihydrogen phosphate and disodium monohydrogen phosphate, as an acid agent.

These pH regulating agents may be alone as an acid agent or as an alkali agent, or both of them may be combined, and the content thereof is preferably 0.01 mass % or more and further 0.1 mass % or more in the hair cosmetic, and is preferably 20 mass % or less and further 15 mass % or less in the hair cosmetic from the viewpoint of decrease of hair damage and scalp stimulation.

[Formulation]

The hair cosmetic of the invention may be formulated in a form such as a liquid form, an emulsion form, a cream form, a gel form, a paste form, a mousse form and an aerosol. Meanwhile, when the hair cosmetic of the invention is of an aerosol, the content of each ingredient and pH of the hair cosmetic as explained before are the content in an undiluted solution not containing a propellant, and pH of the undiluted solution.

The hair cosmetic of the invention can be suitably used for, for example, an in-bath agent such as a pre-shampoo treatment, a shampoo, a hair rinse, a hair conditioner, a hair treatment and a post-shampoo treatment; an out-bath agent such as a non-aerosol foam, an aerosol foam, a hair gel, a hair mousse, a hair mist, a hair lotion, a hair oil and a styling agent; and a bleaching or hair dye composition.

Examples of the bleaching or hair dye composition include an one-agent type hair dye composition, a two-agent type bleaching or hair dye composition, and a three-agent type bleaching or hair dye composition.

The one-agent type hair dye composition is a composition containing a direct dye, and includes products called a hair manicure, an acidic dye, a color rinse and a color treatment as common names. Examples of the product form of the one-agent type hair dye composition include a gel type, a cream type, and an aerosol type.

The two-agent type bleaching or hair dye composition consists of a first agent containing an alkali agent and a second agent containing hydrogen peroxide, and includes products called a hair bleach and a hair dyeing as common names. Examples of the product form of the two-agent type bleaching or hair dye composition include a cream type, an emulsion type, a liquid type, a foam type, and an aerosol type.

The three-agent type bleaching or hair dye composition consists of the first agent and the second agent used in the two-agent type bleaching or hair dye composition, and in addition, further a third agent containing an active ingredient (for example, a persulfate (ammonium persulfate, potassium persulfate, sodium persulfate) for improving decoloring power). Examples of the product form of the three-agent type bleaching or hair dye composition include a cream type, an emulsion type, a liquid type, a foam type, and an aerosol type, similarly to the two-agent type bleaching or hair dye composition.

[Method for Use (Hair Treatment Method)]

Treatment of hair with the hair cosmetic of the invention is performed by bringing hair into contact with the hair cosmetic directly or using a tool. As for the method for the contact, a method that is generally widely used in the type of the hair cosmetic, can be applied.

For example, examples of the method for the contact include, in a case of a pre-shampoo treatment, a method of bringing dry or wet hair into contact with a suitable amount of the pre-shampoo treatment before shampoo treatment, leaving the hair for several seconds to several tens of minutes, and then washing away the pre-shampoo treatment with flowing water; in a case of a shampoo, a method of bringing hair into contact with a suitable amount of the shampoo, massaging the hair for several minutes with bubbling the shampoo, and then washing away the shampoo with flowing water; in a case of such as a hair rinse, a hair conditioner, a hair treatment, and a post-shampoo treatment, a method of subjecting hair to shampoo treatment, and then bringing the hair into contact with a suitable amount of the hair rinse, etc., leaving the hair for seconds to several tens of minutes, and then washing away the hair rinse, etc. with flowing water; and in a case of such as a hair mousse, a hair oil, and a styling agent, a method of bringing hair into contact with a suitable amount of the hair mousse, etc. and leaving the hair as it is. Herein, the suitable amount is such an amount that the bath ratio to the mass of hair is about 1:0.005 to 1:10. The hair to be treated may be a part or the whole thereof. The application temperature to hair is preferably about room temperature to body temperature, but may be heated to about 50° C. in order to enhance the penetration.

When the hair cosmetic of the invention is a bleaching or hair dye composition, for example, the bleaching or hair dye composition may be applied to hair (after the first agent and the second agent in a case of a two-agent type are mixed, or the first agent and the second agent and further the third agent in a case of a three-agent type are mixed right before use), left for a prescribed time, and then washed away using water, and dried. The application temperature to hair is from 15° C. to 45° C., and the application time is from 3 to 60 minutes, further from 5 to 45 minutes and further preferably from 10 to 30 minutes.

With regards to the embodiments described above, preferred aspects of the invention are further disclosed below.

<1> A hair cosmetic comprising the following ingredients (A) and (B):

(A) a cationic polymer having a charge density of 5.0 meq/g or more and 7.0 meq/g or less and (B) an anionic polysaccharide derivative wherein a part of the hydrogen atoms of the hydroxyl group of a polysaccharide compound having a constituent unit represented by the formula (1) are substituted with $-(CH_2)_m COO^-$ group (m is an integer of 1 to 5) at an average substitution degree of 0.5 or more and 2.0 or less per constituent unit, and wherein optionally a part of the hydrogen atoms of the remaining hydroxyl groups are substituted with linear or branched $C_{1-40}$ alkyl groups and/or alkylene groups, wherein the viscosity of the ingredient (B) in a 2 mass % aqueous solution at 25° C. is 0.5 mPa·s or more and 800 mPa·s or less:

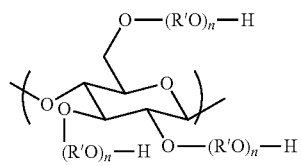

wherein R' may be the same or different, and represents a $C_{2-4}$ linear or branched alkylene group optionally substituted with a hydroxyl group, and n represents a number by which the average number of added moles of R'O per constituent unit is 0 to 10.

<2> The hair cosmetic according to <1>, wherein the ingredient (A) is preferably at least one member selected from the group consisting of a polymer comprising a diallyl quaternary ammonium salt as a constituent unit and a quaternized polyvinyl imidazolium derivative.

<3> The hair cosmetic according to <2>, wherein the polymer comprising a diallyl quaternary ammonium salt as a constituent unit preferably has a backbone represented by the following formula (2) or (3):

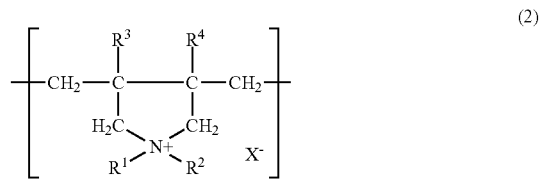

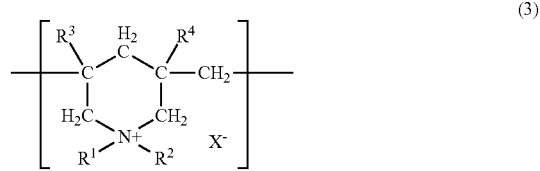

wherein $R^1$ and $R^2$ may be the same or different, and represents a hydrogen atom, a $C_{1-18}$ alkyl group, an aryl group (such as phenyl group), a hydroxyalkyl group, an amidoalkyl group, a cyanoalkyl group, an alkoxyalkyl group or a carboalkoxyalkyl group; $R^3$ and $R^4$ may be the same or different, and represents a hydrogen atom, a $C_{1-3}$ alkyl group or a phenyl group; and $X^-$ represents an anion (for example, a chloride ion, a bromide ion, an iodide ion, a sulfate anion, a sulfonate anion, a methylsulfate anion, a phosphate anion, and a nitrate anion).

<4> The hair cosmetic according to <3>, wherein the polymer comprising a diallyl quaternary ammonium salt as a constituent unit contains the constituent unit represented by the formula (2) or (3) in preferably 65 to 100 mol %, more preferably 75 to 100 mol %, further preferably 90 to 100 mol %, and further preferably 95 to 100 mol % in one molecule.

<5> The hair cosmetic according to any one of <2> to <4>, wherein the polymer comprising a diallyl quaternary ammonium salt as a constituent unit is preferably a homopolymer of a diallyl quaternary ammonium salt or a copolymer of a diallyl quaternary ammonium salt and an acrylic acid.

<6> The hair cosmetic according to <2>, wherein the quaternized polyvinyl imidazolium derivative preferably has a backbone represented by the following formula (6):

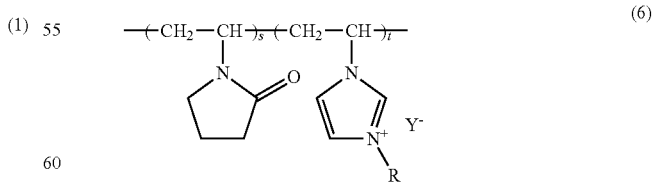

wherein R represents a hydrogen atom or a $C_{1-3}$ alkyl group, $Y^-$ represents an anion such as a chloride ion, a bromide ion, an iodide ion, a sulfate anion, a sulfonate anion, a $C_{1-4}$ alkyl sulfate anion, a phosphate anion and a nitrate anion, and s and t represent molar ratios and s+t=100.

<7> The hair cosmetic according to <6>, wherein t in the formula (6) is preferably 73 or more, more preferably 90 or more and further preferably 93 or more, and is preferably 99 or less.

<8> The hair cosmetic according to any one of <1> to <7>, wherein the weight average molecular weight of the ingredient (A) is preferably 10,000 or more, more preferably 50,000 or more and further preferably 100,000 or more, and is preferably 3,000,000 or less, more preferably 1,000,000 or less and further preferably 800,000 or less.

<9> The hair cosmetic according to any one of <1> to <8>, wherein the content of the ingredient (A) is preferably 0.01 mass % or more, more preferably 0.1 mass % or more, further preferably 0.5 mass % or more and further preferably 0.75 mass % or more, and is preferably 20 mass % or less, more preferably 10 mass % or less, further preferably 5 mass % or less, further preferably 3 mass % or less, further preferably 2.5 mass % or less and further preferably 2 mass % or less.

<10> The hair cosmetic according to any one of <1> to <9>, wherein the polysaccharide compound having a constituent unit represented by the formula (1) in the ingredient (B) is preferably at least one member selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum and hydroxypropylmethyl starch.

<11> The hair cosmetic according to any one of <1> to <10>, wherein the viscosity of the ingredient (B) in a 2 mass % aqueous solution at 25° C. is preferably 1 mPa·s or more and more preferably 2 mPa·s or more, and is preferably 500 mPa·s or less, more preferably 300 mPa·s or less, further preferably 150 mPa·s or less, further preferably 120 mPa·s or less, further preferably 100 mPa·s or less, further preferably 50 mPa·s or less and further preferably 20 mPa·s or less.

<12> The hair cosmetic according to any one of <1> to <11>, wherein the average substitution degree per constituent unit of $-(CH_2)_mCOO^-$ groups in the ingredient (B) is preferably 0.6 or more and more preferably 0.65 or more, and preferably 1.5 or less, more preferably 1.2 or less and further preferably 0.9 or less.

<13> The hair cosmetic according to any one of <1> to <12>, wherein the ingredient (B) is preferably carboxymethyl cellulose.

<14> The hair cosmetic according to any one of <1> to <13>, wherein the hair cosmetic is a bleaching or hair dye composition, and the ingredient (B) is preferably contained in the first agent when the bleaching or hair dye composition is of a two-agent type, or the ingredient (B) is preferably contained in the first agent or the third agent, and more preferably in the third agent when the bleaching or hair dye composition is of a three-agent type.

<15> The hair cosmetic according to any one of <1> to <14>, wherein the content of the ingredient (B) is preferably 0.01 mass % or more, more preferably 0.1 mass % or more, further preferably 0.3 mass % or more and further preferably 0.5 mass % or more, and is preferably 20 mass % or less, more preferably 10 mass % or less, further preferably 5 mass % or less, further preferably 3 mass % or less and further preferably 1.5 mass % or less.

<16> The hair cosmetic according to any one of <1> to <15>, wherein the mass ratio of the ingredient (A) to the ingredient (B), (A)/(B) is preferably 0.1 or more, more preferably 0.2 or more, further preferably 0.3 or more and further preferably 0.5 or more, and is preferably 30 or less, more preferably 15 or less, further preferably 10 or less, further preferably 5 or less, further preferably 3 or less, further preferably 2 or less and further preferably 1.5 or less.

<17> The hair cosmetic according to any one of <1> to <16>, wherein the hair cosmetic preferably further contains a surfactant selected from the group consisting of an anionic surfactant, a nonionic surfactant, a cationic surfactant and an amphoteric surfactant.

<18> The hair cosmetic according to <17>, wherein the content of the surfactant is preferably 0.1 mass % or more, more preferably 0.5 mass % or more and further preferably 1 mass % or more, and is preferably 30 mass % or less, more preferably 25 mass % or less, further preferably 20 mass % or less and further preferably 15 mass % or less.

<19> The hair cosmetic according to any one of <1> to <18>, wherein the hair cosmetic preferably further contains higher alcohol having a carbon number of 12 or more and more preferably 16 or more, and is preferably 30 or less and more preferably 22 or less.

<20> The hair cosmetic according to <19>, wherein the content of the higher alcohol is preferably 3 mass % or more and more preferably 4 mass % or more, and is preferably 11 mass % or less and more preferably 9 mass % or less.

<21> The hair cosmetic according to any one of <1> to <20>, wherein the hair cosmetic preferably further contains a $C_{2-20}$ polyhydric alcohol.

<22> The hair cosmetic according to <21>, wherein the content of the polyhydric alcohol is preferably 0.1 mass % or more, more preferably 0.5 mass % or more and further preferably 1 mass % or more, and is preferably 20 mass % or less, more preferably 15 mass % or less and further preferably 10 mass % or less.

<23> The hair cosmetic according to any one of <1> to <22>, wherein the hair cosmetic preferably further contains a conditioning ingredient selected from silicones and oil.

<24> The hair cosmetic according to <23>, wherein the content of the silicones is preferably 0.1 mass % or more and more preferably 0.5 mass % or more, and is preferably 20 mass % or less and more preferably 15 mass % or less.

<25> The hair cosmetic according to <23>, wherein the content of the oil is preferably 0.1 mass % or more and more preferably 0.5 mass % or more, and is preferably 20 mass % or less and more preferably 15 mass % or less.

<26> The hair cosmetic according to any one of <1> to <25>, wherein the hair cosmetic preferably further contains a polymer for setting.

<27> The hair cosmetic according to <26>, wherein the content of the polymer for setting is preferably 0.1 mass % or more and more preferably 0.5 mass % or more, and is preferably 5 mass % or less and more preferably 3 mass % or less.

<28> The hair cosmetic according to any one of <1> to <27>, wherein the hair cosmetic is preferably selected from the group consisting of a pre-shampoo treatment, a shampoo, a hair rinse, a hair conditioner, a hair treatment, a post-shampoo treatment, a non-aerosol foam, an aerosol foam, a hair gel, a hair mousse, a hair mist, a hair lotion, a hair oil, a styling agent, and a bleaching or hair dye composition.

<29> The hair cosmetic according to any one of <1> to <13> and <15> to <28>, wherein the hair cosmetic is not a bleaching or hair dye composition, and the pH of the hair cosmetic at 25° C. is preferably 2 or more, more preferably 4.5 or more and further preferably 5.5 or more, and is preferably 12 or less, more preferably 11.5 or less and further preferably 11 or less.

<30> The hair cosmetic according to <28> or <29>, wherein the hair cosmetic is a shampoo, and contains an anionic surfactant, and the content thereof is preferably 2 mass % or more, more preferably 2.5 mass % or more, further preferably 3 mass % or more and further preferably 5 mass % or more, and is preferably 30 mass % or less, more preferably 25 mass % or less, further preferably 20 mass % or less and further preferably 15 mass % or less.

<31> The hair cosmetic according to <30>, wherein the mass ratio of the anionic surfactant to the sum of the ingredient (A) and the ingredient (B) (anionic surfactant/ [ingredient (A)+ingredient (B)]) is preferably 0.3 or more, more preferably 0.5 or more, further preferably 1 or more and further preferably 1.5 or more, and is preferably 10 or less, more preferably 8 or less, further preferably 7 or less and further preferably 4 or less.

<32> The hair cosmetic according to <28> or <29>, wherein the hair cosmetic is a hair rinse, a hair conditioner or a hair treatment, and contains a cationic surfactant, and the content thereof is preferably 0.1 mass % or more, more preferably 0.5 mass % or more and further preferably 1.0 mass % or more, and is preferably 15 mass % or less, more preferably 10 mass % or less and further preferably 8 mass % or less.

<33> The hair cosmetic according to <32>, wherein the mass ratio of the cationic surfactant to the sum of the ingredient (A) and the ingredient (B) (cationic surfactant/ [ingredient (A)+ingredient (B)]) is preferably 0.3 or more, more preferably 0.5 or more and further preferably 1 or more, and is preferably 10 or less, more preferably 8 or less, further preferably 6 or less, further preferably 4 or less and further preferably 2 or less.

<34> The hair cosmetic according to <28>, wherein the hair cosmetic is a bleaching or hair dye composition, and the content of the surfactant is preferably 2 mass % or more, more preferably 2.5 mass % or more and further preferably 3 mass % or more, and is preferably 20 mass % or less, more preferably 15 mass % or less, further preferably 10 mass % or less, further preferably 8 mass % or less, further preferably 7 mass % or less and further preferably 6 mass % or less.

<35> A method of treating hair comprising bringing dry or wet (preferably dry) hair into contact with the pre-shampoo treatment of the hair cosmetic described in <28>, leaving the hair, then washing away the pre-shampoo treatment with flowing water, and then subjecting the hair to shampoo treatment.

<36> A method of treating hair comprising bringing hair into contact with a suitable amount of the shampoo of the hair cosmetic described in <28>, massaging the hair with bubbling the shampoo, and then washing away the shampoo with flowing water.

<37> A method of treating hair comprising bringing hair into contact with the hair rinse, the hair conditioner, the hair treatment or the post-shampoo treatment of the hair cosmetic described in <28>, subjecting the hair to shampoo treatment, and then leaving the hair, and then washing away the shampoo with flowing water.

<38> A method of treating hair comprising applying the bleaching or hair dye composition of the hair cosmetic described in <28> to hair, leaving the hair for 3 to 60 minutes at 15° C. to 45° C., and then washing away the bleaching or hair dye composition using water, and drying the hair.

EXAMPLES

Examples 1 to 15 and Comparative Examples 1 to 4

The hair cosmetics shown in Tables 1 to 3 were prepared in accordance with a conventional method. Measurement of the combing force, and evaluations for finger-combing smoothness of wet hair and manageability of dry hair were performed in accordance with the method and the criteria described below.

Method of Treating Hair 10 g of a bundle of Japanese hair (30 cm length) damaged from repetitive bleaches and hair washings was prepared. This was taken as hair before treatment. With respect to this hair, the hair cosmetics according to Described in Tables 1 to 3 (pre-shampoo treatment compositions) were coated onto hair in 1:1 of the bath ratio (mass of hair:mass of aqueous solution), respectively. The hair was rinsed with flowing water, and dried. This was taken as hair immediately after treatment. Further, this hair was subjected to shampoo washing and drying repeatedly 14 times at ordinary conditions. This was taken as the hair after 14 times of shampoo washings.

Evaluation for Physical Property (Test for Combing Force)

In order to perform evaluation for physical properties, the hair bundle treated with the method described above (immediately after treatment and after 14 times of shampoo washings) was hanged on a force gauge, and then the hair tress was clipped with two hair brushes from front and rear or both sides. Combing was performed 15 times, and the force taken at each combing was measured. As the measuring device, the device described in J. Soc. Cosmet. Chem. Japan. Vol. 27, No. 1, P11-13 1993 was used. The combing was performed at a speed of about once/second. With the average value of 10 times of the measurements (maximum value) excluding the first 5 times among the measured combing forces, combability was evaluated. Meanwhile, as the hair brush, Kao Lunette (full length: about 20 cm, comb part size: about 4×10 cm, comb density: 6 pieces/cm) was used. The averages of 10 times of the measurements (maximum value) are shown in Tables 1 to 3.

Sensory Evaluation (Finger-Combing Smoothness of Wet Hair)

The hair bundle treated with the method described above (immediately after treatment and after 14 times of shampoo washings) was wetted with water, and the finger-combing smoothness at the time was sensory-evaluated with the following 5 steps by 10 expert panels. The sum of the points is shown in Tables 1 to 3.

+2: Better finger-combing smoothness than Comparative Example 1

+1: Slightly better finger-combing smoothness than Comparative Example 1

0: Nearly equal finger-combing smoothness to Comparative Example 1

−1: Slightly worse finger-combing smoothness than Comparative Example 1

−2: Worse finger-combing smoothness than Comparative Example 1

Sensory Evaluation (Manageability of Dry Hair)

Manageability (when dried) of the hair bundle treated with the method described above (immediately after treatment and after 14 times of shampoo washings) was sensory-evaluated with the following 5 steps by 10 expert panels. The sum of the points is shown in Tables 1 to 3.

+2: No hair bouncing and better manageability than Comparative Example 1

+1: Slightly better manageability than Comparative Example 1

0: Nearly equal manageability to Comparative Example 1

−1: Slightly worse manageability than Comparative Example 1

−2: A lot of hair bouncing and worse manageability than Comparative Example 1

TABLE 1

| | Ingredient (mass %; active ingredient) | Example 1 | 2 | 3 | 4 | 5 | 6 | 7 | 8 | 9 | 10 |
|---|---|---|---|---|---|---|---|---|---|---|---|
| (A) | Homopolymer of dimethyldiallyl ammonium chloride*1 | 0.74 | 0.74 | 0.74 | 0.74 | 0.74 | 0.74 | — | — | — | 0.74 |
| | Solution of copolymer of dimethyldiallyl ammonium chloride•acrylic acid (95:5)*2 | — | — | — | — | — | — | 0.74 | — | — | — |
| | Solution of copolymer of dimethyldiallyl ammonium chloride•acrylic acid (65:35)*3 | — | — | — | — | — | — | — | 0.74 | — | — |
| | Copolymer of vinylpyrrolidone•N-methylvinyl imidazolinium chloride*4 | — | — | — | — | — | — | — | — | 0.74 | — |
| | Solution of copolymer of dimethyldiallyl ammonium chloride•acrylamide (30:70)*5 | — | — | — | — | — | — | — | — | — | — |
| (B) | Carboxymethyl cellulose (viscosity of 2 mass % aqueous solution; 3 mPa·s)*6 | 1.26 | — | — | — | — | — | 1.22 | 1.02 | 1.24 | 1.26 |
| | Carboxymethyl cellulose (viscosity of 2 mass % aqueous solution; 17 mPa·s)*7 | — | 1.26 | — | — | — | — | — | — | — | — |
| | Carboxymethyl cellulose (viscosity of 2 mass % aqueous solution; 135 mPa·s)*8 | — | — | 1.10 | — | — | — | — | — | — | — |
| | Carboxymethyl cellulose (viscosity of 2 mass % aqueous solution; 298 mPa·s)*9 | — | — | — | 1.04 | — | — | — | — | — | — |
| | Carboxymethylhydroxyethyl cellulose (viscosity of 2 mass % aqueous solution; 100 mPa·s)*10 | — | — | — | — | 1.26 | — | — | — | — | — |
| | Carboxymethylmethyl cellulose (viscosity of 2 mass % aqueous solution; 100 mPa·s)*11 | — | — | — | — | — | 1.26 | — | — | — | — |
| | Carboxymethyl cellulose (viscosity of 2 weight % aqueous solution; 835 mPa·s)*12 | — | — | — | — | — | — | — | — | — | — |
| Others | Sodium chloride | 2.0 | 2.0 | 2.0 | 2.0 | 2.0 | 2.0 | 2.0 | 2.0 | 2.0 | 2.0 |
| | pH regulating agent (sodium hydroxide) | Suitable amount | Suitable amount | Suitable amount | Suitable amount | Suitable amount | Suitable amount | Suitable amount | Suitable amount | Suitable amount | Suitable amount |
| | Purified water | Balance | Balance | Balance | Balance | Balance | Balance | Balance | Balance | Balance | Balance |
| Total | | 100 | 100 | 100 | 100 | 100 | 100 | 100 | 100 | 100 | 100 |
| pH | | 6.0 | 6.0 | 6.0 | 6.0 | 6.0 | 6.0 | 6.0 | 6.0 | 6.0 | 6.0 |
| Mass ratio of (A)/(B) | | 0.59 | 0.59 | 0.67 | 0.71 | 0.59 | 0.59 | 0.61 | 0.73 | 0.60 | 0.59 |
| Physical property Evaluation | Combing force (g) Immediately after treatment | 165 | 183 | 212 | 225 | 241 | 258 | 189 | 191 | 212 | 162 |
| | After 14 times of shampoo washings | 281 | 317 | 342 | 382 | 383 | 398 | 289 | 303 | 351 | 275 |
| Sensory Evaluation | Finger-combing smoothness (Wet hair) Immediately after treatment | 16 | 14 | 13 | 12 | 11 | 10 | 15 | 13 | 12 | 16 |
| | After 14 times of shampoo washings | 14 | 12 | 11 | 10 | 9 | 9 | 14 | 12 | 11 | 14 |
| | Manageability (Dry hair) Immediately after treatment | 17 | 13 | 12 | 11 | 10 | 9 | 16 | 12 | 12 | 17 |
| | After 14 times of shampoo washings | 15 | 11 | 10 | 9 | 8 | 7 | 14 | 10 | 9 | 15 |

TABLE 2

| | Ingredient (mass %; active ingredient) | Example 11 | 12 | 13 | 14 | 15 |
|---|---|---|---|---|---|---|
| (A) | Homopolymer of dimethyldiallyl ammonium chloride*1 | 0.37 | 1.11 | 1.48 | 0.74 | 0.74 |
| | Solution of copolymer of dimethyldiallyl ammonium chloride•acrylic acid (95:5)*2 | — | — | — | — | — |
| | Solution of copolymer of dimethyldiallyl ammonium chloride•acrylic acid (65:35)*3 | — | — | — | — | — |
| | Copolymer of vinylpyrrolidone•N-methylvinyl imidazolinium chloride*4 | — | — | — | — | — |
| | Solution of copolymer of dimethyldiallyl ammonium chloride•acrylamide (30:70)*5 | — | — | — | — | — |

TABLE 2-continued

|  | Ingredient (mass %; active ingredient) | | Example | | | | |
|---|---|---|---|---|---|---|---|
|  | | | 11 | 12 | 13 | 14 | 15 |
| (B) | Carboxymethyl cellulose (viscosity of 2 mass % aqueous solution; 3 mPa·s)*6 | | 0.63 | 1.89 | 2.52 | 0.97 | 2.18 |
|  | Carboxymethyl cellulose (viscosity of 2 mass % aqueous solution; 17 mPa·s)*7 | | — | — | — | — | — |
|  | Carboxymethyl cellulose (viscosity of 2 mass % aqueous solution; 135 mPa·s)*8 | | — | — | — | — | — |
|  | Carboxymethyl cellulose (viscosity of 2 mass % aqueous solution; 298 mPa·s)*9 | | — | — | — | — | — |
|  | Carboxymethylhydroxyethyl cellulose (viscosity of 2 mass % aqueous solution; 100 mPa·s)*10 | | — | — | — | — | — |
|  | Carboxymethylmethyl cellulose (viscosity of 2 mass % aqueous solution; 100 mPa·s)*11 | | — | — | — | — | — |
|  | Carboxymethyl cellulose (viscosity of 2 weight % aqueous solution; 835 mPa·s)*12 | | — | — | — | — | — |
| Others | Sodium chloride | | 2.0 | 2.0 | 2.0 | 2.0 | 2.0 |
|  | pH regulating agent (sodium hydroxide) | | Suitable amount | Suitable amount | Suitable amount | Suitable amount | Suitable amount |
|  | Purified water | | Balance | Balance | Balance | Balance | Balance |
| Total | | | 100 | 100 | 100 | 100 | 100 |
| pH | | | 6.0 | 6.0 | 6.0 | 6.0 | 6.0 |
| Mass ratio of (A)/(B) | | | 0.59 | 0.59 | 0.59 | 0.76 | 0.34 |
| Physical property Evaluation | Combing force (g) | Immediately after treatment | 176 | 181 | 179 | 175 | 189 |
|  | | After 14 times of shampoo washings | 292 | 294 | 293 | 289 | 294 |
| Sensory Evaluation | Finger-combing smoothness (Wet hair) | Immediately after treatment | 15 | 15 | 15 | 15 | 15 |
|  | | After 14 times of shampoo washings | 12 | 12 | 12 | 12 | 12 |
|  | Manageability (Dry hair) | Immediately after treatment | 15 | 16 | 16 | 16 | 15 |
|  | | After 14 times of shampoo washings | 13 | 13 | 13 | 14 | 12 |

TABLE 3

|  | Ingredient (mass %; active ingredient) | | Comparative Example | | | |
|---|---|---|---|---|---|---|
|  | | | 1 | 2 | 3 | 4 |
| (A) | Homopolymer of dimethyldiallyl ammonium chloride*1 | | 0.74 | 0.74 | — | — |
|  | Solution of copolymer of dimethyldiallyl ammonium chloride•acrylic acid (95:5)*2 | | — | — | — | — |
|  | Solution of copolymer of dimethyldiallyl ammonium chloride•acrylic acid (65:35)*3 | | — | — | — | — |
|  | Copolymer of vinylpyrrolidone•N-methylvinyl imidazolinium chloride*4 | | — | — | — | — |
|  | Solution of copolymer of dimethyldiallyl ammonium chloride•acrylamide (30:70)*5 | | — | — | 0.74 | 0.74 |
| (B) | Carboxymethyl cellulose (viscosity of 2 mass % aqueous solution; 3 mPa·s)*6 | | — | — | 0.63 | — |
|  | Carboxymethyl cellulose (viscosity of 2 mass % aqueous solution; 17 mPa·s)*7 | | — | — | — | — |
|  | Carboxymethyl cellulose (viscosity of 2 mass % aqueous solution; 135 mPa·s)*8 | | — | — | — | — |
|  | Carboxymethyl cellulose (viscosity of 2 mass % aqueous solution; 298 mPa·s)*9 | | — | — | — | — |
|  | Carboxymethylhydroxyethyl cellulose (viscosity of 2 mass % aqueous solution; 100 mPa·s)*10 | | — | — | — | — |
|  | Carboxymethylmethyl cellulose (viscosity of 2 mass % aqueous solution; 100 mPa·s)*11 | | — | — | — | — |
|  | Carboxymethyl cellulose (viscosity of 2 weight % aqueous solution; 835 mPa·s)*12 | | — | 1.26 | — | 0.63 |
| Others | Sodium chloride | | 2.0 | 2.0 | 2.0 | 2.0 |
|  | pH regulating agent (sodium hydroxide) | | Suitable amount | Suitable amount | Suitable amount | Suitable amount |
|  | Purified water | | Balance | Balance | Balance | Balance |
| Total | | | 100 | 100 | 100 | 100 |
| pH | | | 6.0 | 6.0 | 6.0 | 6.0 |
| Mass ratio of (A)/(B) | | | — | 0.59 | 1.2 | 1.17 |
| Physical property Evaluation | Combing force (g) | Immediately after treatment | 445 | 398 | 364 | 426 |
|  | | After 14 times of shampoo washings | 521 | 517 | 516 | 524 |
| Sensory | Finger-combing smoothness | Immediately after treatment | 0 | −2 | 2 | −3 |

TABLE 3-continued

|  |  | Comparative Example | | | |
|---|---|---|---|---|---|
| Ingredient (mass %; active ingredient) | | 1 | 2 | 3 | 4 |
| Evaluation (Wet hair) | After 14 times of shampoo washings | 0 | 0 | 0 | 0 |
| Manageability (Dry hair) | Immediately after treatment | 0 | 0 | 1 | −2 |
|  | After 14 times of shampoo washings | 0 | 0 | 0 | 0 |

*1: Merquat 100 (manufactured by Lubrizol Advanced Materials, Inc., having 6.2 meq/g of charge density)
*2: Merquat 295 (manufactured by Lubrizol Advanced Materials, Inc., having 6.0 meq/g of charge density)
*3: Merquat 280 (manufactured by Lubrizol Advanced Materials, Inc., having 5.0 meq/g of charge density)
*4: Luviquat Excellence (manufactured by BASF, having 6.1 meq/g of charge density)
*5: Merquat 550 (manufactured by Lubrizol Advanced Materials, Inc., having 3.1 meq/g of charge density)
*6: CELLOGEN F-5A (manufactured by DKS Co. Ltd., having 0.7 of substitution degree)
*7: CELLOGEN F-7A (manufactured by DKS Co. Ltd., having 0.7 of substitution degree)
*8: CELLOGEN F-815A (manufactured by DKS Co. Ltd., having 0.8 of substitution degree)
*9: CELLOGEN F-930A (manufactured by DKS Co. Ltd., having 0.85 of substitution degree)
*10: Manufactured in accordance with JP A H9-110901 (0.77 of substitution degree)
*11: Manufactured in accordance with JP A H9-110901 (0.77 of substitution degree)
*12: CELLOGEN F-SA (manufactured by DKS Co. Ltd., having 0.7 of substitution degree)

In each of the formulation examples described below, the content is an amount as an active ingredient.

| Formulation Example 1 (shampoo) | (mass %) |
|---|---|
| Carboxymethyl cellulose*1 | 0.50 |
| Dimethyldiallyl ammonium chloride•acrylic acid copolymer*2 | 0.30 |
| Polyoxyethylene (2) lauryl ether sodium sulfate | 11.0 |
| Polyoxypropylene (3) octyl ether | 1.0 |
| Mono 2-ethylhexylglyceryl ether | 1.0 |
| Lauryl hydroxysulfobetaine | 2.0 |
| Polyoxyethylene (6) stearyl ether | 2.0 |
| Lauric acid | 0.8 |
| Dipotassium glycyrrhizinate | 0.1 |
| Coconut oil fatty acid monoethanol amide | 1.0 |
| Lauric acid amidopropyl betaine | 0.5 |
| Dimethylpolysiloxane*3 | 1.5 |
| Aminopolyether-modified silicone*4 | 0.2 |
| Ethylene glycol distearyl ester | 1.5 |
| Dipropylene glycol | 3.0 |
| Benzyl oxyethanol | 0.5 |
| 1-Menthol | 1.0 |
| Sodium chloride | 1.0 |
| Flavor | Suitable amount |
| pH regulating agent (sodium hydroxide) | Amount to pH 5.0 |
| Purified water | Balance |
| Total | 100 |

*1CELLOGEN F-7A (DKS Co. Ltd.)
*2Merquat 295 having 6.0 meq/g of charge density manufactured by Lubrizol Advanced Materials, Inc.
*3Silicone CF2450 (Dow Corning Toray Co., Ltd.)
*4Silicone SILSTYLE 104 Dow Corning Toray Co., Ltd.)

| Formulation Example 2 (Hair treatment) | (mass %) |
|---|---|
| Carboxymethyl cellulose*1 | 0.25 |
| Copolymer of diallyldimethyl ammonium chloride•acrylic acid*2 | 0.15 |
| Stearic acid dimethylaminopropyl amide | 1.0 |
| Behenyl alcohol | 4.0 |
| Stearyl alcohol | 3.0 |
| Benzyl alcohol | 1.0 |
| Polypropylene glycol (molecular weight 300) | 1.0 |
| Behenyltrimethyl ammonium chloride | 1.5 |
| High molecular weight methylpolysiloxane*3 | 2.0 |
| Squalene | 1.0 |
| Hydroxyethyl cellulose (Mw = 500, 000) | 0.3 |
| Isononyl isononate | 1.0 |
| Fatty acid ester of dipentaerythritol*4 | 0.3 |
| Casein hydrolysate | 0.1 |
| Aloe essence | 0.1 |
| Methyl paraben | 0.1 |
| Rice germ oil | 0.6 |
| L-glutamic acid | 0.5 |
| Flavor | 0.4 |
| Purified water | Balance |
| Total | 100 |

*1CELLOGEN F-7A (DKS Co. Ltd.)
*2Merquat 295 having 6.0 meq/g of charge density, manufactured by Lubrizol Advanced Materials, Inc.
*3BY11-003 (Dow Corning Toray Co., Ltd.)
*4COSMOL 168M (The Nisshin OilliO Group, Ltd.)

| Formulation Example 3 (Hair gel) | (mass %) |
|---|---|
| Carboxymethyl cellulose*1 | 0.50 |
| Diallyl dimethyl ammonium chloride•acrylic acid copolymer*2 | 0.30 |
| Ethanol | 10.0 |
| Glycerin | 2.0 |
| Dipropylene glycol | 2.0 |
| Benzyl alcohol | 0.5 |
| PEG-60 hydrogenated castor oil | 0.3 |
| (C12-14) s-PARETH-9 | 1.0 |
| Stearyltrimethyl ammonium chloride | 0.25 |
| Hydroxyethyl cellulose | 2.0 |
| Hexyldiethylaminohydroxybenzoyl benzoate*3 | 0.01 |
| Sodium chloride | 1.0 |
| Flavor | 0.05 |
| pH regulating agent (Caustic potassium) | Amount to pH 5.0 |
| Purified water | Balance |
| Total | 100 |

*1CELLOGEN F-7A (DKS Co. Ltd.)
*2Merquat 295 having 6.0 meq/g of charge density, manufactured by Lubrizol Advanced Materials, Inc.
*3Uvinul A PLUS (BASF)

| Formulation Example 4 (aerosol foam) <Undiluted solution> | (mass %) |
|---|---|
| Carboxymethyl cellulose*1 | 0.25 |
| Diallyl dimethyl ammonium chloride•acrylicacid copolymer*2 | 0.15 |
| Ethanol | 4.5 |

-continued

| Formulation Example 4 (aerosol foam) <Undiluted solution> | (mass %) |
|---|---|
| Glycerin | 1.0 |
| Dipropylene glycol | 2.0 |
| Benzyl alcohol | 0.2 |
| (C12-14) s-PARETH-9 | 1.0 |
| Polyoxyethylene lauryl ether (16E.O.) | 1.0 |
| Stearyltrimethyl ammonium chloride | 0.25 |
| Hexyldiethylaminohydroxybenzoyl benzoate*[3] | 0.01 |
| Flavor | 0.05 |
| pH regulating agent (Caustic potassium) | Amount to pH 5.0 |
| Purified water | Balance |
| Total | 100 |

*[1]CELLOGEN F-7A (DKS Co. Ltd.)
*[2]Merquat 295 having 6.0 meq/g of charge density, manufactured by Lubrizol Advanced Materials, Inc.
*[3]Uvinul A PLUS (BASF)

<Propellant>
LPG (0.44 MPa)
<Ratio of Undiluted Solution/Propellant>
93.0/7.0

| Formulation Example 5 (non-aerosol foamer) | (mass %) |
|---|---|
| Carboxymethyl cellulose*[1] | 0.20 |
| Diallyl dimethyl ammonium chloride•acrylic acid copolymer*[2] | 0.15 |
| Ethanol | 11.0 |
| Dipropylene glycol | 2.0 |
| Benzyl alcohol | 0.2 |
| Polysilicone-9 | 2.0 |
| PEG-32 | 1.0 |
| PEG-400 | 1.0 |
| (C12-14) s-PARETH-9 | 1.0 |
| Stearyltrimethyl ammonium chloride | 0.25 |
| PEG-60 hydrogenated castor oil | 0.3 |
| PPG-10 sorbitol | 1.0 |
| CETETH-20 | 0.5 |
| Hexyldiethylaminohydroxybenzoyl benzoate*[3] | 0.01 |
| Flavor | 0.05 |
| pH regulating agent (Caustic potassium) | Amount to pH 5.0 |
| Purified water | Balance |
| Total | 100 |

*[1]CELLOGEN F-7A (DKS Co. Ltd.)
*[2]Merquat 295 having 6.0 meq/g of charge density, manufactured by Lubrizol Advanced Materials, Inc.
*[3]Uvinul A PLUS (BASF)

Examples 16 to 31 and Comparative Examples 5 to 8

The first agent shown in Table 4 (pH (25° C.)=10.2), the second agent shown in Table 5 (common) (pH (25° C.)=3.4) and the third agent shown in Table 6 (pH (25° C.)=5.7) were prepared with a conventional method, respectively (pH (25° C.) of the mixed solution of the first agent, the second agent and the third agent was 10.5). Finger-combing smoothness at the time of rinsing (immediately after hair dyeing and passing of time after hair dyeing) and glossy feeling after hair drying (immediately after hair dyeing and passing of time after hair dyeing) were evaluated in accordance with the methods and the criteria described below by 10 panels. The sums of the points are shown in Tables 7 and 8.

In addition, combing force at the time of rinsing (immediately after hair dyeing and passing of time after hair dyeing) was also measured, and shown in Tables 7 and 8.

<Finger-Combing Smoothness at the Time of Rinsing (Immediately after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, and then rinsed with flowing water. Finger-combing smoothness at the time of rinsing after shampoo was sensory-evaluated with the following 5 steps in comparison to Comparative Example 5.

+2: Better finger-combing smoothness than Comparative Example 5
+1: Slightly better finger-combing smoothness than Comparative Example 5
0: Nearly equal finger-combing smoothness to Comparative Example 5
−1: Slightly worse finger-combing smoothness than Comparative Example 5
−2: Worse finger-combing smoothness than Comparative Example <Glossy Feeling after Hair Drying (Immediately after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, rinsed with flowing water, treated with a conditioner, rinsed with flowing water and dried. Glossy feeling after the hair drying was sensory-evaluated with the following 5 steps in comparison to Comparative Example 5.

+2: More glossy than Comparative Example 5
+1: Slightly more glossy than Comparative Example 5
0: Nearly equally glossy to Comparative Example 5
−1: Slightly less glossy than Comparative Example 5
−2: Less glossy than Comparative Example 5

<Finger-Combing Smoothness when Rinsing (Passing of Time after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, rinsed with flowing water, treated with a conditioner, rinsed with flowing water and dried. Then, the hair was rinsed with flowing water, washed with a shampoo, rinsed with flowing water, treated with a conditioner, rinsed and dried. These procedures were repeated 14 times. The finger-combing smoothness at the time of the 15th rinsing with flowing water was sensory-evaluated with the following 5 steps in comparison to Comparative Example 5.

+2: Better finger-combing smoothness than Comparative Example 5
+1: Slightly better finger-combing smoothness than Comparative Example 5
0: Nearly equal finger-combing smoothness to Comparative Example 5
−1: Slightly worse finger-combing smoothness than Comparative Example 5
−2: Worse finger-combing smoothness than Comparative Example 5

<Glossy Feeling after Hair Drying (Passing of Time after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, rinsed with flowing water, treated with a conditioner, rinsed with flowing water and dried. Then, the hair was rinsed with flowing water, washed with a shampoo, treated with a conditioner, rinsed and dried. These procedures were repeated 14 times. Then, the glossy feeling of the hair sensory-evaluated with the following 5 steps in comparison to Comparative Example 5.

+2: More glossy than Comparative Example 5
+1: Slightly more glossy than Comparative Example 5
0: Nearly equally glossy to Comparative Example 5
−1: Slightly less glossy than Comparative Example 5
−2: Less glossy than Comparative Example 5

<Combing Force at the Time of Rinsing (Immediately after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, and then rinsed with flowing water. In order to evaluate combing force at the time of rinsing after shampoo washing, the treated hair was hanged on a force gauge, and then the hair tress was clipped with two hair brushes from front and rear or both sides. Combing was performed 30 times, and the force taken at each combing was measured. As the measuring device, the device described in J. Soc. Cosmet. Chem. Japan. Vol. 27, No. 1, P11-13 1993 was used. The combing was performed at a speed of about once/second. With the average value of 25 times of the measurement (maximum value) excluding the first 5 times among the measured combing forces, combing force was evaluated. Meanwhile, as the hair brush, Kao Lunette (full length: about 20 cm, comb part size: about 4×10 cm, comb density: 6 pieces/cm) was used.

<Combing Force at the Time of Rinsing (Passing of Time after Hair Dyeing)>

5 g of the first agent, 5 g of the second agent and 1 g of the third agent were well mixed, and coated onto 10 g of Japanese hair that had been subjected to cosmetic treatment such as bleach, and left for 30 minutes. Then, the hair was rinsed with flowing water, washed with a shampoo, and then rinsed with flowing water and dried. These procedures were repeated, and the combing force at the time of the 15th rinsing after shampoo washing was measured using a similar method to the combing force at the time of rinsing (Immediately after hair dyeing).

TABLE 4

| First agent | (mass %) |
| --- | --- |
| Cationic polymer (Tables 7 and 8) | Tables 7 and 8 |
| Solution of toluene-2, 5-diamine (20 mass %) | 2.5 |

TABLE 4-continued

| First agent | (mass %) |
| --- | --- |
| Resorcin | 0.4 |
| p-aminophenol | 0.1 |
| m-aminophenol | 0.2 |
| 2-Methyl-5-aminophenol | 0.1 |
| Polyethylene glycol | 4.0 |
| 18-Methyleicosanoic acid | 2.0 |
| Solution of ammonium dialkyl(12-18) dimethyl chloride (75 mass %, QUARTAMIN D2345P, Kao Corporation) | 0.2 |
| Ammonium octadecylpropyl-N, N, N-trimethyl chloride | 5.5 |
| Polyoxyethylene (2) cetyl ether | 0.8 |
| Polyoxyethylene (40) cetyl ether | 2.2 |
| Stearyl alcohol | 6.0 |
| Behenyl alcohol | 1.6 |
| Mixture of dimethicone/(aminoethylaminopropyl methicone/dimethicone) copolymer (Silicone CF1046, Dow Corning Toray Co., Ltd.) | 1.5 |
| Liquid paraffin | 2.0 |
| Dried sodium sulfite | 0.4 |
| Ascorbic acid | 0.4 |
| Tetrasodium edetate dihydrate | 0.1 |
| Monoethanolamine | 1.0 |
| Strong ammonia water (28 mass %) | 7.5 |
| Guanidine carbonate | 5.0 |
| Flavor | 0.7 |
| Purified water | Balance |
| Total | 100 |

TABLE 5

| Second agent | (mass %) |
| --- | --- |
| Hydrogen peroxide solution (35 mass %) | 16.3 |
| Polyoxyethylene (40) cetyl ether | 2.0 |
| Polyoxyethylene (2) cetyl ether | 1.8 |
| Behenyl alcohol | 4.3 |
| Stearyl alcohol | 1.8 |
| Liquid paraffin | 10.0 |
| Concentrated glycerin | 3.0 |
| Trimethyl glycine | 1.0 |
| Oxyquinoline sulfate | 0.05 |
| Hydroxyethane diphosphonic acid | 0.08 |
| Purified water | Balance |
| Total | 100 |

TABLE 6

| Third agent | (mass %) |
| --- | --- |
| Anionic polysaccharide derivative (Tables 7 and 8) | Tables 7 and 8 |
| Purified water | Balance |
| Total | 100 |

TABLE 7

| | | | Example | | | | | | | | | |
| --- | --- | --- | --- | --- | --- | --- | --- | --- | --- | --- | --- | --- |
| | | | 16 | 17 | 18 | 19 | 20 | 21 | 22 | 23 | 24 | 25 |
| Content of each polymer in First agent or third agent (active ingredient) | | | | | | | | | | | | |
| (A) First agent (A) (mass %) | | Homopolymer of dimethyldiallyl ammonium chloride*[1] | 1.7 | 1.7 | 1.7 | 1.7 | 1.7 | 1.7 | 0.85 | 2.6 | 1.7 | 1.7 |
| | | Solution of copolymer of dimethyldiallyl ammonium chloride•acrylic acid (95:5)*[2] | — | — | — | — | — | — | — | — | — | — |

TABLE 7-continued

|  |  |  | Example |  |  |  |  |  |  |  |  |  |
|---|---|---|---|---|---|---|---|---|---|---|---|---|
|  |  |  | 16 | 17 | 18 | 19 | 20 | 21 | 22 | 23 | 24 | 25 |
| (A) |  | Solution of copolymer of dimethyldiallyl ammonium chloride•acrylic acid (65:35)*3 | — | — | — | — | — | — | — | — | — | — |
| (A) |  | Copolymer of vinyl pyrrolidone•N-methylvinyl imidazolinium chloride*4 | — | — | — | — | — | — | — | — | — | — |
| (A') |  | Solution of copolymer of dimethyldiallyl ammonium chloride•acrylamide (30:70)*5 | — | — | — | — | — | — | — | — | — | — |
| (B) | Third agent (mass %) | Carboxymethyl cellulose (viscosity of 2 mass % aqueous solution; 3 mPa · s)*6 | 13.5 | — | — | — | — | — | 6.7 | 20.6 | 11.0 | 16.5 |
| (B) |  | Carboxymethyl cellulose (viscosity of 2 mass % aqueous solution; 17 mPa · s)*7 | — | 13.5 | — | — | — | — | — | — | — | — |
| (B) |  | Carboxymethyl cellulose (viscosity of 2 mass % aqueous solution; 135 mPa · s)*8 | — | — | 12.3 | — | — | — | — | — | — | — |
| (B) |  | Carboxymethyl cellulose (viscosity of 2 mass % aqueous solution; 298 mPa · s)*9 | — | — | — | 11.7 | — | — | — | — | — | — |
| (B) |  | Carboxymethylhydroxyethyl cellulose (viscosity of 2 mass % aqueous solution; 100 mPa · s)*10 | — | — | — | — | 20.5 | — | — | — | — | — |
| (B) |  | Carboxymethylmethyl cellulose (viscosity of 2 mass % aqueous solution; 100 mPa · s)*11 | — | — | — | — | — | 14.9 | — | — | — | — |
| (B') |  | Carboxymethyl cellulose (viscosity of 2 weight % aqueous solution; 835 mPa · s)*12 | — | — | — | — | — | — | — | — | — | — |
| Contents of Ingredient (A) and Ingredient (B) in hair dye composition after mixing (active ingredient) |  |  |  |  |  |  |  |  |  |  |  |  |
| Content of Ingredient (A) (mass %) |  |  | 0.77 | 0.77 | 0.77 | 0.77 | 0.77 | 0.77 | 0.39 | 1.18 | 0.77 | 0.77 |
| Content of Ingredient (B) (mass %) |  |  | 1.23 | 1.23 | 1.12 | 1.06 | 1.86 | 1.35 | 0.61 | 1.87 | 1.00 | 1.50 |
| Mass ratio of (A)/(B) |  |  | 0.63 | 0.63 | 0.69 | 0.73 | 0.41 | 0.57 | 0.63 | 0.63 | 0.77 | 0.52 |
| Evaluation | Finger-combing smoothness when rinsing (immediately after hair dyeing) |  | 16 | 14 | 13 | 12 | 11 | 11 | 14 | 15 | 16 | 16 |
|  | Finger-combing smoothness when rinsing (passing of time after hair dyeing) |  | 17 | 12 | 11 | 11 | 10 | 10 | 15 | 18 | 17 | 17 |
|  | Glossy feeling after hair drying (immediately after hair dyeing) |  | 18 | 14 | 13 | 12 | 11 | 10 | 13 | 16 | 18 | 18 |
|  | Glossy feeling after hair drying (passing of time after hair dyeing) |  | 15 | 12 | 11 | 11 | 10 | 9 | 12 | 15 | 15 | 15 |
|  | Combing force (g) when rinsing (immediately after hair dyeing) |  | 248 | 280 | 295 | 300 | 320 | 328 | 270 | 250 | 247 | 248 |
|  | Combing force (g) when rinsing (passing of time after hair dyeing) |  | 280 | 315 | 330 | 350 | 360 | 371 | 298 | 270 | 281 | 280 |

TABLE 8

|  |  |  | Example |  |  |  |  | Comparative Example |  |  |  |
|---|---|---|---|---|---|---|---|---|---|---|---|
|  |  |  | 26 | 27 | 28 | 29 | 30 | 31 | 5 | 6 | 7 | 8 |
| Content of each polymer in First agent or third agent (active ingredient) |  |  |  |  |  |  |  |  |  |  |  |  |
| (A) | First agent (mass %) | Homopolymer of dimethyldiallyl ammonium chloride*1 | — | — | — | — | — | — | 1.7 | 1.7 | — | — |
| (A) |  | Solution of copolymer of dimethyldiallyl ammonium chloride•acrylic acid (95:5)*2 | 1.7 | 1.7 | — | — | — | — | — | — | — | — |
| (A) |  | Solution of copolymer of dimethyldiallyl ammonium chloride•acrylic acid (65:35)*3 | — | — | 1.7 | 1.7 | — | — | — | — | — | — |

TABLE 8-continued

|  |  |  | Example | | | | | | Comparative Example | | | |
|---|---|---|---|---|---|---|---|---|---|---|---|---|
|  |  |  | 26 | 27 | 28 | 29 | 30 | 31 | 5 | 6 | 7 | 8 |
| (A) |  | Copolymer of vinyl pyrrolidone•N-methylvinyl imidazolinium chloride*4 | — | — | — | — | 1.7 | 1.7 | — | — | — | — |
| (A') |  | Solution of copolymer of dimethyldiallyl ammonium chloride•acrylamide (30:70)*5 | — | — | — | — | — | — | — | — | 1.7 | 1.7 |
| (B) | Third agent (mass %) | Carboxymethyl cellulose (viscosity of 2 mass % aqueous solution; 3 mPa · s)*6 | 13.0 | — | 10.9 | — | 13.3 | — | — | — | 6.7 | — |
| (B) |  | Carboxymethyl cellulose (viscosity of 2 mass % aqueous solution; 17 mPa · s)*7 | — | — | — | — | — | — | — | — | — | — |
| (B) |  | Carboxymethyl cellulose (viscosity of 2 mass % aqueous solution; 135 mPa · s)*8 | — | — | — | — | — | — | — | — | — | — |
| (B) |  | Carboxymethyl cellulose (viscosity of 2 mass % aqueous solution; 298 mPa · s)*9 | — | 11.3 | — | 9.4 | — | 11.5 | — | — | — | — |
| (B) |  | Carboxymethylhydroxyethyl cellulose (viscosity of 2 mass % aqueous solution; 100 mPa · s)*10 | — | — | — | — | — | — | — | — | — | — |
| (B) |  | Carboxymethylmethyl cellulose (viscosity of 2 mass % aqueous solution; 100 mPa · s)*11 | — | — | — | — | — | — | — | — | — | — |
| (B') |  | Carboxymethyl cellulose (viscosity of 2 weight % aqueous solution; 835 mPa · s)*12 | — | — | — | — | — | — | — | 13.5 | — | 6.7 |
| Contents of Ingredient (A) and Ingredient (B) in hair dye composition after mixing (active ingredient) | | | | | | | | | | | | |
| Content of Ingredient (A) or (A') (mass %) | | | 0.77 | 0.77 | 0.77 | 0.77 | 0.77 | 0.77 | 0.77 | 0.77 | 0.77 | 0.77 |
| Content of Ingredient (B) or (B') (mass %) | | | 1.18 | 1.03 | 0.99 | 0.85 | 1.21 | 1.05 | 0 | 1.23 | 0.61 | 0.61 |
| Mass ratio of [(A) or (A')]/[(B) or (B')] | | | 0.65 | 0.75 | 0.78 | 0.90 | 0.64 | 0.74 | — | 0.63 | 1.27 | 1.27 |
| Evaluation | Finger-combing smoothness when rinsing (immediately after hair dyeing) | | 16 | 12 | 14 | 12 | 13 | 12 | 0 | −2 | 2 | −4 |
|  | Finger-combing smoothness when rinsing (passing of time after hair dyeing) | | 17 | 11 | 15 | 11 | 11 | 11 | 0 | 0 | 0 | 0 |
|  | Glossy feeling after hair drying (immediately after hair dyeing) | | 18 | 12 | 13 | 12 | 13 | 12 | 0 | 0 | 1 | −2 |
|  | Glossy feeling after hair drying (passing of time after hair dyeing) | | 15 | 11 | 12 | 11 | 11 | 11 | 0 | 0 | 0 | 0 |
|  | Combing force (g) when rinsing (immediately after hair dyeing) | | 248 | 305 | 270 | 302 | 295 | 300 | 404 | 410 | 398 | 420 |
|  | Combing force (g) when rinsing (passing of time after hair dyeing) | | 285 | 355 | 295 | 351 | 330 | 350 | 440 | 440 | 440 | 440 |

*1: Merquat 100 (manufactured by Lubrizol Advanced Materials, Inc., having 6.2 meq/g of charge density)
*2: Merquat 295 (manufactured by Lubrizol Advanced Materials, Inc., having 6.0 meq/g of charge density)
*3: Merquat 280 (manufactured by Lubrizol Advanced Materials, Inc., having 5.0 meq/g of charge density)
*4: Luviquat Excellence (manufactured by BASF, having 6.1 meq/g of charge density)
*5: Merquat 550 (manufactured by Lubrizol Advanced Materials, Inc., having 3.1 meq/g of charge density)
*6: CELLOGEN F-5A (manufactured by DKS Co. Ltd., having 0.7 of substitution degree)
*7: CELLOGEN F-7A (manufactured by DKS Co. Ltd., having 0.7 of substitution degree)
*8: CELLOGEN F-815A (manufactured by DKS Co. Ltd., having 0.8 of substitution degree)
*9: CELLOGEN F-930A (manufactured by DKS Co. Ltd., having 0.85 of substitution degree)
*10: Manufactured in accordance with JP A H9-110901 (0.77 of substitution degree)
*11: Manufactured in accordance with JP A H9-110901 (0.77 of substitution degree)
*12: CELLOGEN F-SA (manufactured by DKS Co. Ltd., having 0.7 of substitution degree)

Formulation Example 6 (Two-Agent Type Hair Dye) First Agent:Second Agent=1:1 (Mass Ratio)

| First agent (cream) | (mass %) |
|---|---|
| Strong ammonia water (28 mass %) | 1.5 |
| Monoethanol amine | 3.0 |
| Ammonium bicarbonate | 0.5 |
| Solution of copolymer of dimethyldiallyl ammonium chloride•acrylic acid (40 mass %)*1 | 4.0 |

| First agent (cream) | (mass %) |
|---|---|
| Carboxymethyl cellulose*³ | 2.7 |
| Amodimethicone (40 mass % emulsion)*² | 1.0 |
| High molecular weight dimethylpolysiloxane (2700 of number average polymerization degree) | 1.5 |
| Dimethylpolysiloxane (550 of number average polymerization degree) | 4.0 |
| Cetostearyl alcohol | 7.0 |
| Octyl dodecanol | 1.0 |
| Polyoxyethylene (40) cetyl ether | 2.0 |
| Polyoxyethylene (2) cetyl ether | 1.0 |
| Solution of stearyltrimethyl ammonium chloride (28 mass %) | 3.0 |
| Solution of dialkyl (12-18) dimethyl ammonium chloride (75 mass %) | 0.5 |
| Propylene glycol | 3.0 |
| Tetrasodium edetate | 0.1 |
| Ascorbic acid | 0.3 |
| Sodium sulfite | 0.5 |
| p-phenylene diamine | 0.4 |
| Toluene-2, 5-diamine | 0.4 |
| Para-aminophenol | 0.5 |
| Metha-aminophenol | 0.2 |
| 2-Methyl-5-aminophenol | 0.1 |
| Resorcin | 0.4 |
| Flavor | 0.5 |
| Purified water | Balance |
| Total | 100 |

*¹Merquat 295 (Lubrizol Advanced Materials, Inc.)
*²Silicone SM8704C (Dow Corning Toray Co., Ltd.)
*³CELLOGEN F-5A (DKS Co. Ltd.)

| Second agent (cream) | (mass %) |
|---|---|
| Hydrogen peroxide water (35 mass %) | 16.2 |
| 8-Quinolinol sulfate | 0.04 |
| Polyoxyethylene (40) cetyl ether | 1.0 |
| Polyoxyethylene (2) cetyl ether | 1.0 |
| Cetostearyl alcohol | 3.5 |
| Phosphoric acid | Amount to pH 3.5 |
| Purified water | Balance |
| Total | 100 |

Formulation Example 7 (Two-Agent Type Hair Dye) First Agent:Second Agent=1:1 (Mass Ratio), Gel Form after Mixing

| First agent (gel form) | (mass %) |
|---|---|
| Strong ammonia water (28 mass %) | 5.0 |
| Solution of polydimethylmethylene piperidinium chloride (40 mass %)*¹ | 4.0 |
| Carboxymethyl cellulose*² | 2.7 |
| Oleic acid | 5.0 |
| Octyl dodecanol | 1.0 |
| Polyoxyethylene (10) nonylphenyl ether | 20.0 |
| Polyethylene glycol | 20.0 |
| Sodium sulfite | 0.5 |
| p-phenylene diamine | 2.0 |

| First agent (gel form) | (mass %) |
|---|---|
| Ortho-aminophenol | 0.5 |
| Resorcin | 0.5 |
| Flavor | 0.1 |
| Purified water | Balance |
| Total | 100 |

*¹Merquat 100 (Lubrizol Advanced Materials, Inc.)
*²CELLOGEN F-7A (DKS Co. Ltd.)

| Second agent (liquid form) | (mass %) |
|---|---|
| Hydrogen peroxide water (35 mass %) | 15.0 |
| Tetrasodium edetate | 0.5 |
| Cetanol | 2.0 |
| Sodium laurylsulfate | 0.5 |
| Phenacetin | 0.1 |
| Purified water | Balance |
| Total | 100 |

| Formulation Example 8 (acidic hair dye) | (mass %) |
|---|---|
| Black No. 401 | 0.2 |
| Violet No. 401 | 0.3 |
| Yellow No. 4 | 0.3 |
| Benzyl alcohol | 4.0 |
| Citric acid | 0.3 |
| Solution of copolymer of dimethyldiallyl ammonium chloride•acrylic acid (40 mass %)*¹ | 2.0 |
| Carboxymethyl cellulose*² | 1.2 |
| N-stearoyl-N-methyl taurine sodium salt | 20.0 |
| Stearyl alcohol | 8.0 |
| Dimethylpolysiloxane (6 cs) | 2.0 |
| Emulsion polymer of dimethylpolysiloxane | 2.0 |
| Flavor | 0.1 |
| Purified water | Balance |
| Total | 100 |

*¹Merquat 295 (Lubrizol Advanced Materials, Inc.)
*²CELLOGEN F-7A (DKS Co. Ltd.)

| Formulation Example 9 (color rinse containing acidic dye) | (mass %) |
|---|---|
| Black No. 401 | 0.03 |
| Violet No. 401 | 0.01 |
| Yellow No. 4 | 0.01 |
| Benzyl alcohol | 3.0 |
| Dipropylene glycol | 15.0 |
| Citric acid | 1.5 |
| Solution of polydimethylmethylene piperidinium chloride (40 mass %)*¹ | 2.0 |
| Carboxymethyl cellulose*² | 1.2 |
| Methylphenyl polysiloxane | 4.0 |
| Polyoxyethylene hydrogenated castor oil EO40 | 1.0 |
| Hydroxyethyl cellulose | 2.5 |
| Purified water | Balance |
| Total | 100 |

*¹Merquat 100 (Lubrizol Advanced Materials, Inc.)
*²CELLOGEN F-5A (DKS Co. Ltd.)

| Formulation Example 10 (color rinse containing basic dye) | (mass %) |
|---|---|
| Cetyltrimethyl ammonium chloride | 1.00 |
| Cetostearyl alcohol | 2.75 |
| Coconut monoethanol amide | 1.00 |
| Paraffin wax | 1.00 |
| Basic Blue-99 | 0.15 |
| Solution of copolymer of dimethyldiallyl ammonium chloride•acrylic acid (40 mass %)*[1] | 2.0 |
| Carboxymethyl cellulose*[2] | 1.2 |
| Basic Brown 16 | 0.03 |
| HC Blue 2 | 0.15 |
| Disperse Violet 4 | 0.20 |
| Flavor | 0.70 |
| Preservative | 0.25 |
| pH regulating agent | Suitable amount |
| Purified water | Balance |
| Total | 100 |

*[1]Merquat 100 (Lubrizol Advanced Materials, Inc.)
*[2]CELLOGEN F-5A (DKS Co. Ltd.)

The invention claimed is:

1. A hair cosmetic comprising ingredients (A) and (B):
(A) from 0.37 to 5 mass % of a cationic polymer having a charge density of 5.0 meq/g or more and 6.2 meq/g or less; and
(B) from 0.61 to 2.52 mass % of an anionic polysaccharide derivative wherein a part of the hydrogen atoms of the hydroxyl group of a polysaccharide compound having a constituent unit represented by formula (1) are substituted with $-(CH_2)_mCOO^-$ group, wherein m is an integer of 1 to 5, at an average substitution degree of from 0.7 to 0.85 per constituent unit, and wherein optionally a part of the hydrogen atoms of the remaining hydroxyl groups are substituted with linear or branched $C_{1-40}$ alkyl groups, alkylene groups, or a combination thereof;
wherein:
a mass ratio of ingredient (A) to ingredient (B), (A)/(B), is from 0.2 to 1.5;
a viscosity of ingredient (B) in a 2 mass % aqueous solution at 25° C. is from 3 mPa·s to 298 mPa·s; and
formula (1) is:

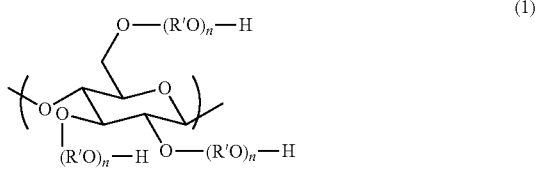
(1)

wherein each R', independently, represents a $C_{2-4}$ linear alkylene group optionally substituted with a hydroxyl group or a $C_{2-4}$ branched alkylene group optionally substituted with a hydroxyl group, and n represents a number by which the average number of added moles of R'O per constituent unit is 0 to 10.

2. The hair cosmetic according to claim 1, wherein ingredient (A) is at least one selected from the group consisting of a polymer comprising a diallyl quaternary ammonium salt as a constituent unit and a polymer comprising quaternized vinyl imidazolium as a constituent unit.

3. The hair cosmetic according to claim 2, wherein the polymer comprising a diallyl quaternary ammonium salt as a constituent unit is a homopolymer of a diallyl quaternary ammonium salt or a copolymer of a diallyl quaternary ammonium salt and an acrylic acid.

4. The hair cosmetic according to claim 1, wherein the polysaccharide compound having a constituent unit represented by formula (1) in ingredient (B) is at least one member selected from the group consisting of cellulose, guar gum, starch, hydroxyethyl cellulose, hydroxyethyl guar gum, hydroxyethyl starch, methyl cellulose, methyl guar gum, methyl starch, ethyl cellulose, ethyl guar gum, ethyl starch, hydroxypropyl cellulose, hydroxypropyl guar gum, hydroxypropyl starch, hydroxyethylmethyl cellulose, hydroxyethylmethyl guar gum, hydroxyethylmethyl starch, hydroxypropylmethyl cellulose, hydroxypropylmethyl guar gum, and hydroxypropylmethyl starch.

5. The hair cosmetic according to claim 1, wherein
ingredient (B) is present in a first agent when the hair cosmetic is a two-agent bleaching composition or a two-agent hair dye composition, or
ingredient (B) is present in a third agent when the hair cosmetic is a three-agent bleaching composition or a three-agent hair dye composition.

6. The hair cosmetic according to claim 1, wherein the mass ratio of ingredient (A) to ingredient (B), (A)/(B), is from 0.34 to 0.76.

7. The hair cosmetic according to claim 1, wherein the charge density of ingredient (A) is from 5.5 meq/g to 6.2 meq/g.

8. The hair cosmetic according to claim 1, wherein ingredient (B) is carboxymethyl cellulose.

9. The hair cosmetic according to claim 1, wherein the weight average molecular weight of ingredient (A) is from 10,000 to 3,000,000.

10. The hair cosmetic according to claim 1, further comprising a surfactant selected from the group consisting of an anionic surfactant, a nonionic surfactant, a cationic surfactant and an amphoteric surfactant.

* * * * *